United States Patent
Liao et al.

(10) Patent No.: US 8,143,036 B2
(45) Date of Patent: Mar. 27, 2012

(54) GENETICALLY MODIFIED MICROORGANISMS FOR PRODUCING ITACONIC ACID WITH HIGH YIELDS

(75) Inventors: James C. Liao, Los Angeles, CA (US); Pei-Ching Chang, Hsinchu County (TW)

(73) Assignee: Industrial Technology Research Institute, Hsin Chu (TW)

( * ) Notice: Subject to any disclaimer, the term of this patent is extended or adjusted under 35 U.S.C. 154(b) by 347 days.

(21) Appl. No.: 12/463,677

(22) Filed: May 11, 2009

(65) Prior Publication Data

US 2010/0285546 A1    Nov. 11, 2010

(51) Int. Cl.
C12P 7/46 (2006.01)
C12P 21/06 (2006.01)
C12P 19/34 (2006.01)
C12N 1/20 (2006.01)
C12N 9/88 (2006.01)
C12N 9/10 (2006.01)
C12N 9/00 (2006.01)
C12N 15/00 (2006.01)
C07H 21/04 (2006.01)

(52) U.S. Cl. ............. 435/145; 435/252.3; 435/232; 435/193; 435/183; 435/69.1; 435/91.1; 435/320.1; 536/23.1; 536/23.2; 536/23.7; 536/23.74

(58) Field of Classification Search .......... 435/145, 435/252.3, 232, 193, 183, 69.1, 91.1, 320.1; 536/23.1, 23.2, 23.7, 23.74
See application file for complete search history.

(56) References Cited

U.S. PATENT DOCUMENTS

| 7,479,381 B1 | 1/2009 | Kuo et al. |
| 2007/0105938 A1* | 5/2007 | Anderson et al. ............ 514/419 |
| 2008/0038787 A1* | 2/2008 | Zelder et al. ................ 435/115 |

FOREIGN PATENT DOCUMENTS

| EP | 2 017 344 | 1/2009 |
| JP | 2008-182936 | 8/2008 |
| JP | 2009-027999 | 2/2009 |
| WO | WO 2009/014437 | 1/2009 |

OTHER PUBLICATIONS

Bradbury et al., The second aconitase (AcnB) of *Escherichia coli*. Microbiol., 1996, vol. 142: 389-400.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Shin Kanamasa et al., "Cloning and Functional Characterization of the *cis*-aconitic acid decarboxylase (CAD) gene from *Aspergillus terreus*"; Applied Microbiology and Biotechnology, vol. 80, No. 2, pp. 223-229 (2008).

* cited by examiner

*Primary Examiner* — Ganapathirama Raghu
(74) *Attorney, Agent, or Firm* — Occhiuti Rohlicek & Tsao LLP

(57) ABSTRACT

Genetically modified microorganisms that produce itaconic acid at high yields and uses thereof.

22 Claims, No Drawings

GENETICALLY MODIFIED MICROORGANISMS FOR PRODUCING ITACONIC ACID WITH HIGH YIELDS

BACKGROUND OF THE INVENTION

Itaconic acid, an essential precursor to various products (e.g., acrylic fibers, rubbers, artificial diamonds, and lens), is in high demand in the chemical industry. Conventionally, itaconic acid is isolated from *Aspergillus terreus*. However, *A. terreus* grows slowly and does not produce itaconic acid in its spore-forming stage. There is a need for a method that produces itaconic acid in high yield.

SUMMARY OF THE INVENTION

The present invention is based on the unexpected discovery that certain genetically modified *E. coli* strains produce itaconic acid at much higher levels relative to wild-type *E. coli* strains.

In one aspect, this invention features a genetically modified microorganism containing (i) a mutated endogenous icd gene that expresses a lower level of isocitrate dehydrogenase compared with its wild-type counterpart and (ii) an exogenous nucleotide sequence encoding a cis-aconitic acid decarboxylase (CAD) operably linked to a suitable promoter (i.e., capable of initiating gene transcription in the microorganism). The modified microorganism can be *Aspergillus niger, Aspergillus terreus, Escherichia coli, Pseudozyma Antarctica, Yarrowia lipotica*, or *Saccharomyces cerevisiae*. It can further contain at least one exogenous nucleotide sequences encoding one of the following three enzymes: (a) an enzyme that converts phosphoenolpyruvate to oxaloacetate (i.e., phosphoenolpyruvate carboxylase; also known as phosphoenolpyruvate carboxykinase), (b) an enzyme that converts oxaloacetate to citrate (i.e., citrate synthase, 2-methylcitrate synthase, and citrate lyase), and (c) an enzyme that converts citrate or isocitrate to cis-aconitic acid (i.e., aconitase and 2-methylcitrate dehydratase). Each of these exogenous nucleotide sequences is operably linked to a suitable promoter.

In another aspect, this invention features a genetically modified microorganism containing (i) a first exogenous nucleotide sequence encoding CAD, (ii) a second exogenous nucleotide sequence encoding enzyme (a) or enzyme (b) mentioned above, and optionally (iii) a third exogenous nucleotide sequence encoding enzyme (c) also mentioned above. Alternatively, the microorganism contains (i) a first exogenous nucleotide sequence encoding CAD, (ii) a second exogenous nucleotide sequence encoding enzyme (a), (iii) a third exogenous nucleotide encoding enzyme (b), and optionally (iv) a fourth exogenous nucleotide sequence encoding enzyme (c). Each of the exogenous nucleotide sequences is linked operatively to a promoter that drives its expression in the microorganism.

Also within the scope of this invention is a method for producing itaconic acid in any of the genetically modified microorganisms described above. This method includes cultivating the genetically modified microorganism in a medium to produce itaconic acid and collecting the medium for isolation of the itaconic acid thus produced. In one example, the medium contains glucose, as the substrate for making itaconic acid, at a concentration ranging from 5-80 g/L (e.g., 10-40 g/L). In another example, the medium contains citrate, as the substrate for making itaconic acid, at a concentration ranging from 5-80 g/L (e.g., 10-40 g/L). When citrate is used as the substrate, the genetically modified microorganism is preferred to be permeabilized.

The details of one or more embodiments of the invention are set forth in the description below. Other features or advantages of the present invention will be apparent from the following detailed description of several embodiments and also from the appended claims.

DETAILED DESCRIPTION OF THE INVENTION

Disclosed herein is a genetically modified microorganism that overly expresses a cis-aconitic acid decarboxylase (CAD), an enzyme that converts cis-aconitic acid to itaconic acid. Examples of the microorganism include, but are not limited to, *Aspergillus, Citrobacter, Corynebacterium, Dekkera, Enterobacter, Enterococcus, Escherichia, Erwinia, Klebsiella, Kluyveromyces, Lactobacillus, Lactococcus, Morganella, Pantoea, Pectobacterium, Penicillium, Pichia, Proteus, Pseudomonas, Pseudozyma, Rhodotorula, Salmonella, Serratia, Shigella, Saccharomyces, Ustilago*, and *Yarrow*.

The term "cis-aconitic acid decarboxylase" or "CAD" used herein refers to any naturally occurring CADs (e.g., the *A. terreus* CAD described in Dwiarti et al., J. Bioscience and Bioengineering, 94 (1):29-33, 2002 and WO 2009/014437) and functional equivalents thereof. Provided below are the nucleotide sequence (SEQ ID NO:1) and amino acid sequence (SEQ ID NO:2) of an exemplary *A. terreus* CAD:

```
A. terreus Cis-aconitic Acid Decarboxylase
atgaccaagcagtctgctgattccaacgcgaagtctggtgtgacctctgagatctgtcac   (SEQ ID NO: 1)
 M  T  K  Q  S  A  D  S  N  A  K  S  G  V  T  S  E  I  C  H    (SEQ ID NO: 2)

tgggcgtctaatctcgccactgatgatatcccgagcgacgttctggagcgtgcaaaatac
 W  A  S  N  L  A  T  D  D  I  P  S  D  V  L  E  R  A  K  Y ctgatcctggatggtatcgcgtgcgcgtgggtaggtgctcgtgtcccatggtctgaaaaa
 L  I  L  D  G  I  A  C  A  W  V  G  A  R  V  P  W  S  E  K tacgttcaagcgaccatgtctttcgaacctccgggtgcgtgtcgtgtcatcggttacggc
 Y  V  Q  A  T  M  S  F  E  P  P  G  A  C  R  V  I  G  Y  G cagaaactgggtccggtagcggctgccatgacgaactctgcatttattcaggcgaccgaa
 Q  K  L  G  P  V  A  A  A  M  T  N  S  A  F  I  Q  A  T  E ctcgatgactatcactctgaagcgccgctgcattccgcgtctatcgttctcccggcagtt
 L  D  D  Y  H  S  E  A  P  L  H  S  A  S  I  V  L  P  A  V ttcgcggcgagcgaagtactggccgaacagggtaaaaccatctctggtattgacgtgatt
 F  A  A  S  E  V  L  A  E  Q  G  K  T  I  S  G  I  D  V  I ctggctgcgatcgttggtttcgagagcggtcctcgcatcggcaaagcgatctacggttct
 L  A  A  I  V  G  F  E  S  G  P  R  I  G  K  A  I  Y  G  S
```

-continued

```
gacctcctgaacaacggctggcactgcggtgcggtatatggcgcaccggctggtgcgctc
 D   L   L   N   N   G   W   H   C   G   A   V   Y   G   A   P   A   G   A   L gcaactggtaagctcctgggcctcacgccggacagcatggaagatgcactgggtattgcc
 A   T   G   K   L   L   G   L   T   P   D   S   M   E   D   A   L   G   I   A tgcacgcaagcatgcggcctcatgtccgcgcagtatggtggcatggttaaacgtgttcag
 C   T   Q   A   C   G   L   M   S   A   Q   Y   G   G   M   V   K   R   V   Q cacggtttcgcagcgcgtaatggtctcctcggtggcctcctggctcacggcggctacgag
 H   G   F   A   A   R   N   G   L   L   G   G   L   L   A   H   G   G   Y   E gcgatgaaaggtgttctcgagcgttcttacggtggcttcctgaagatgttcaccaagggc
 A   M   K   G   V   L   E   R   S   Y   G   G   F   L   K   M   F   T   K   G aacggtcgtgaaccgccgtacaaagaagaagaggttgtggctggtctgggtagcttctgg
 N   G   R   E   P   P   Y   K   E   E   E   V   V   A   G   L   G   S   F   W cacaccttcaccattcgtatcaaactgtacgcgtgctgcggtctcgtacacggtcctgtt
 H   T   F   T   I   R   I   K   L   Y   A   C   C   G   L   V   H   G   P   V gaagccattgaaaacctccagggtcgttacccggaactgctcaatcgtgctaacctgtct
 E   A   I   E   N   L   Q   G   R   Y   P   E   L   L   N   R   A   N   L   S aacatccgccacgttcacgtacaactctctaccgcgagcaactcccactgtggttggatc
 N   I   R   H   V   H   V   Q   L   S   T   A   S   N   S   H   C   G   W   I ccagaagagcgcccaatctcttctatcgcgggtcaaatgtctgtcgcatatatcctcgcc
 P   E   E   R   P   I   S   S   I   A   G   Q   M   S   V   A   Y   I   L   A gttcagctcgttgaccaacagtgtctgctcagccagttctccgagtttgacgataatctg
 V   Q   L   V   D   Q   Q   C   L   L   S   Q   F   S   E   F   D   D   N   L gaacgcccggaagtgtgggacctggcacgtaaggttaccagctctcaatctgaggagttc
 E   R   P   E   V   W   D   L   A   R   K   V   T   S   S   Q   S   E   E   F gaccaggacggtaactgtctctctgccggtcgcgtccgtattgagttcaacgacggctcc
 D   Q   D   G   N   C   L   S   A   G   R   V   R   I   E   F   N   D   G   S tccatcaccgaatccgttgagaagccgctcggtgtaaaggaaccaatgccaaatgaacgc
 S   I   T   E   S   V   E   K   P   L   G   V   K   E   P   M   P   N   E   R atcctgcacaaataccgtaccctggcgggttctgtaacggacgaaagccgtgttaaggag
 I   L   H   K   Y   R   T   L   A   G   S   V   T   D   E   S   R   V   K   E atcgaggatctcgtgctcggcctggaccgtctgaccgatattagcccgctcctcgagctg
 I   E   D   L   V   L   G   L   D   R   L   T   D   I   S   P   L   L   E   L Ctgaattgtccggttaaatccccactggtttaa
 L   N   C   P   V   K   S   P   L   V   -
```

As used herein, a functional equivalent of a reference enzyme (i.e., the *A. terreus* CAD or any of the enzymes mentioned below) is a polypeptide having an amino acid sequence at least 60% (e.g., 85%, 90%, or 95%) identical to that of the reference enzyme and possessing the same enzymatic activity as the reference enzyme.

The percent identity of two amino acid sequences is determined using the algorithm of Karlin and Altschul *Proc. Natl. Acad. Sci.* USA 87:2264-68, 1990, as modified in Karlin and Altschul *Proc. Natl. Acad. Sci.* USA 90:5873-77, 1993. Such an algorithm is incorporated into the BLASTN and BLASTX programs (version 2.0) of Altschul, et al. *J. Mol. Biol.* 215: 403-10, 1990. BLAST protein searches can be performed with the BLASTX program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25:3389-3402, 1997. When utilizing BLAST and Gapped BLAST programs, the default parameters of the respective programs (e.g., BLASTX and BLASTN) can be used.

The genetically modified microorganism described above can have a mutated endogenous icd gene (encoding isocitrate decarboxylase) so that it expresses a lower level of isocitrate decarboxylase as compared with its wild-type counterpart. Isocitrate decarboxylase converts isocitrate to α-ketoglutarate. Icd gene exists in various types of microorganisms, including *Aspergillus terreus* (GenBank Accession Nos. XM_001210553 and XP_001210553), *Citrobacter koseri* (GenBank Accession No. YP_001453397), *Lactobacillus fermentum* (GenBank Accession Nos. NC_009792 and YP_001843755), *Saccharomyces cerevisiae* (GenBank Accession Nos. NC_001146 and NP_014361), *Yarrowia lipolytica* (GenBank Accession Nos. XM_503571 and XP_503571), and *Escherichia coli* (GenBank Accession Nos. NC_000913 and NP_415654) As an example, the coding region of the *E. coli* icd gene is shown below:

```
Nucleotide Sequence and Encoded Amino Acid Sequence of
E. coli Icd gene
atggaaagtaaagtagttgttccggcacaaggcaagaagatcaccctgcaaaacggcaaa   (SEQ ID NO: 3)
 M   E   S   K   V   V   V   P   A   Q   G   K   K   I   T   L   Q   N   G   K   (SEQ ID NO: 4)
```

-continued

```
ctcaacgttcctgaaaatccgattatcccttacattgaaggtgatggaatcggtgtagat
 L  N  V  P  E  N  P  I  I  P  Y  I  E  G  D  G  I  G  V  D gtaaccccagccatgctgaaagtggtcgacgctgcagtcgagaaagcctataaaggcgag
 V  T  P  A  M  L  K  V  V  D  A  A  V  E  K  A  Y  K  G  E cgtaaaatctcctggatggaaatttacaccggtgaaaaatccacacaggtttatggtcag
 R  K  I  S  W  M  E  I  Y  T  G  E  K  S  T  Q  V  Y  G  Q gacgtctggctgcctgctgaaactcttgatctgattcgtgaatatcgcgttgccattaaa
 D  V  W  L  P  A  E  T  L  D  L  I  R  E  Y  R  V  A  I  K ggtccgctgaccactccggttggtggcggtattcgctctctgaacgttgccctgcgccag
 G  P  L  T  T  P  V  G  G  G  I  R  S  L  N  V  A  L  R  Q gaactggatctctacatctgcctgcgtccggtacgttactatcagggcactccaagcccg
 E  L  D  L  Y  I  C  L  R  P  V  R  Y  Y  Q  G  T  P  S  P gttaaacaccctgaactgaccgatatggttatcttccgtgaaaactcggaagacatttat
 V  K  H  P  E  L  T  D  M  V  I  F  R  E  N  S  E  D  I  Y gcgggtatcgaatggaaagcagactctgccgacgccgagaaagtgattaaattcctgcgt
 A  G  I  E  W  K  A  D  S  A  D  A  E  K  V  I  K  F  L  R gaagagatgggggtgaagaaaattcgcttcccggaacattgtggtatcggtattaagccg
 E  E  M  G  V  K  K  I  R  F  P  E  H  C  G  I  G  I  K  P tgttcggaagaaggcaccaaacgtctggttcgtgcagcgatcgaatacgcaattgctaac
 C  S  E  E  G  T  K  R  L  V  R  A  A  I  E  Y  A  I  A  N gatcgtgactctgtgactctggtgcacaaaggcaacatcatgaagttcaccgaaggagcg
 D  R  D  S  V  T  L  V  H  K  G  N  I  M  K  F  T  E  G  A tttaaagactggggctaccagctggcgcgtgaagagtttggcggtgaactgatcgacggt
 F  K  D  W  G  Y  Q  L  A  R  E  E  F  G  G  E  L  I  D  G ggcccgtggctgaaagttaaaaacccgaacactggcaaagagatcgtcattaaagacgtg
 G  P  W  L  K  V  K  N  P  N  T  G  K  E  I  V  I  K  D  V attgctgatgcattcctgcaacagatcctgctgcgtccggctgaatatgatgttatcgcc
 I  A  D  A  F  L  Q  Q  I  L  L  R  P  A  E  Y  D  V  I  A tgtatgaacctgaacggtgactacatttctgacgccctggcagcgcaggttggcggtatc
 C  M  N  L  N  G  D  Y  I  S  D  A  L  A  A  Q  V  G  G  I ggtatcgcccctggtgcaaacatcggtgacgaatgcgccctgtttgaagccacccacggt
 G  I  A  P  G  A  N  I  G  D  E  C  A  L  F  E  A  T  H  G actgcgccgaaatatgccggtcaggacaaagtaaatcctggctctattattctctccgct
 T  A  P  K  Y  A  G  Q  D  K  V  N  P  G  S  I  I  L  S  A gagatgatgctgcgccacatgggttggaccgaagcggctgacttaattgttaaaggtatg
 E  M  M  L  R  H  M  G  W  T  E  A  A  D  L  I  V  K  G  M gaaggcgcaatcaacgcgaaaaccgtaacctatgacttcgagcgtctgatggatggcgct
 E  G  A  I  N  A  K  T  V  T  Y  D  F  E  R  L  M  D  G  A Aaactgctgaaatgttcagagtttggtgacgcgatcatcgaaaacatgtaa
 K  L  L  K  C  S  E  F  G  D  A  I  I  E  N  M  -
```

Methods for producing a microorganism with a mutated endogenous icd gene are well known in the art. For example, mutations (e.g., insertion, deletion, site mutation) of the icd gene can be introduced by homologous recombination.

Alternatively or in addition, the genetically modified microorganism also overly expresses one or more of the following enzymes: (a) an enzyme that converts phosphoenolpyruvate to oxaloacetate (i.e., phosphoenolpyruvate carboxylase/carboxykinase; including three isoforms EC 4.1.1.32, EC 4.1.1.38, and EC 4.1.1.49), (b) an enzyme that converts oxaloacetate to citrate (i.e., citrate synthase, 2-methylcitrate synthase, and citrate lyase), and (c) an enzyme that converts citrate or isocitrate to cis-aconitic acid (i.e., aconitase and 2-methylcitrate dehydratase).

The terms "phosphoenolpyruvate carboxylase/carboxykinase," "citrate synthase," "2-methylcitrate synthase," "citrate lyase," "aconitase," and "2-methylcitrate dehydratase" used herein refers to all enzymes that possess the enzymatic activity described above, including both naturally-occurring enzymes and their functional equivalents. Provided below are nucleotide sequences and amino acid sequences of E. coli phosphoenolpyruvate carboxylase (encoded by ppc gene), citrate synthase (encoded by gltA gene), aconitase A (encoded by acnA gene), and aconitase B (encoded by acnB gene):

```
E. coli Phosphoenolpyruvate Carboxylase
atgaacgaacaatattccgcattgcgtagtaatgtcagtatgctcggcaaagtgctggga  (SEQ ID NO: 5)
 M  N  E  Q  Y  S  A  L  R  S  N  V  S  M  L  G  K  V  L  G    (SEQ ID NO: 6)
```

-continued

```
gaaaccatcaaggatgcgttgggagaacacattcttgaacgcgtagaaactatccgtaag
 E  T  I  K  D  A  L  G  E  H  I  L  E  R  V  E  T  I  R  K ttgtcgaaatcttcacgcgctggcaatgatgctaaccgccaggagttgctcaccaccta
 L  S  K  S  S  R  A  G  N  D  A  N  R  Q  E  L  L  T  T  L caaaatttgtcgaacgacgagctgctgcccgttgcgcgtgcgtttagtcagttcctgaac
 Q  N  L  S  N  D  E  L  L  P  V  A  R  A  F  S  Q  F  L  N ctggccaacaccgccgagcaataccacagcatttcgccgaaaggcgaagctgccagcaac
 L  A  N  T  A  E  Q  Y  H  S  I  S  P  K  G  E  A  A  S  N ccggaagtgatcgcccgcaccctgcgtaaactgaaaaaccagccggaactgagcgaagac
 P  E  V  I  A  R  T  L  R  K  L  K  N  Q  P  E  L  S  E  D accatcaaaaaagcagtggaatcgctgtcgctggaactggtcctcacggctcacccaacc
 T  I  K  K  A  V  E  S  L  S  L  E  L  V  L  T  A  H  P  T gaaattacccgtcgtacactgatccacaaaatggtggaagtgaacgcctgttaaaaacag
 E  I  T  R  R  T  L  I  H  K  M  V  E  V  N  A  C  L  K  Q ctcgataacaaagatatcgctgactacgaacacaaccagctgatgcgtcgcctgcgccag
 L  D  N  K  D  I  A  D  Y  E  H  N  Q  L  M  R  R  L  R  Q ttgatcgcccagtcatggcataccgatgaaatccgtaagctgcgtccaagcccggtagat
 L  I  A  Q  S  W  H  T  D  E  I  R  K  L  R  P  S  P  V  D gaagccaaatgggctttgccgtagtggaaaacagcctgtggcaaggcgtaccaaattac
 E  A  K  W  G  F  A  V  V  E  N  S  L  W  Q  G  V  P  N  Y ctgcgcgaactgaacgaacaactggaagagaacctcggctacaaactgcccgtcgaattt
 L  R  E  L  N  E  Q  L  E  E  N  L  G  Y  K  L  P  V  E  F gttccggtccgttttacttcgtggatgggcggcgaccgcgacgcaacccgaacgtcact
 V  P  V  R  F  T  S  W  M  G  G  D  R  D  G  N  P  N  V  T gccgatatcacccgccacgtcctgctactcagccgctggaaagccaccgatttgttcctg
 A  D  I  T  R  H  V  L  L  L  S  R  W  K  A  T  D  L  F  L aaagatattcaggtgctggtttctgaactgtcgatggttgaagcgacccctgaactgctg
 K  D  I  Q  V  L  V  S  E  L  S  M  V  E  A  T  P  E  L  L gcgctggttggcgaagaaggtgccgcagaaccgtatcgctatctgatgaaaaacctgcgt
 A  L  V  G  E  E  G  A  A  E  P  Y  R  Y  L  M  K  N  L  R tctcgcctgatggcgacacaggcatggctggaagcgcgcctgaaaggcgaagaactgcca
 S  R  L  M  A  T  Q  A  W  L  E  A  R  L  K  G  E  E  L  P aaaccagaaggcctgctgacacaaaacgaagaactgtgggaaccgctctacgcttgctac
 K  P  E  G  L  L  T  Q  N  E  E  L  W  E  P  L  Y  A  C  Y cagtcacttcaggcgtgtggcatgggtattatcgccaacggcgatctgctcgacaccctg
 Q  S  L  Q  A  C  G  M  G  I  I  A  N  G  D  L  L  D  T  L cgccgcgtgaaatgtttcggcgtaccgctggtccgtattgatatccgtcaggagagcacg
 R  R  V  K  C  F  G  V  P  L  V  R  I  D  I  R  Q  E  S  T cgtcataccgaagcgctgggcgagctgacccgctacctcggtatcggcgactacgaaagc
 R  H  T  E  A  L  G  E  L  T  R  Y  L  G  I  G  D  Y  E  S tggtcagaggccgacaaacaggcgttcctgatccgcgaactgaactccaaacgtccgctt
 W  S  E  A  D  K  Q  A  F  L  I  R  E  L  N  S  K  R  P  L ctgccgcgcaactggcaaccaagcgccgaaacgcgcgaagtgctcgatacctgccaggtg
 L  P  R  N  W  Q  P  S  A  E  T  R  E  V  L  D  T  C  Q  V attgccgaagcaccgcaaggctccattgccgcctacgtgatctcgatggcgaaaacgccg
 I  A  E  A  P  Q  G  S  I  A  A  Y  V  I  S  M  A  K  T  P tccgacgtactggctgtccacctgctgctgaaagaagcgggtatcgggtttgcgatgccg
 S  D  V  L  A  V  H  L  L  L  K  E  A  G  I  G  F  A  M  P gttgctccgctgtttgaaaccctcgatgatctgaacaacgccaacgatgtcatgacccag
 V  A  P  L  F  E  T  L  D  D  L  N  N  A  N  D  V  M  T  Q ctgctcaatattgactggtatcgtggcctgattcagggcaaacagatggtgatgattggc
 L  L  N  I  D  W  Y  R  G  L  I  Q  G  K  Q  M  V  M  I  G tattccgactcagcaaaagatgcgggagtgatggcagcttcctgggcgcaatatcaggca
 Y  S  D  S  A  K  D  A  G  V  M  A  A  S  W  A  Q  Y  Q  A
```

```
caggatgcattaatcaaaacctgcgaaaaagcgggtattgagctgacgttgttccacggt
 Q  D  A  L  I  K  T  C  E  K  A  G  I  E  L  T  L  F  H  G cgcggcggttccattggtcgcggcggcgcacctgctcatgcggcgctgctgtcacaaccg
 R  G  G  S  I  G  R  G  G  A  P  A  H  A  A  L  L  S  Q  P ccaggaagcctgaaaggcggcctgcgcgtaaccaacagggcgagatgatccgctttaaa
 P  G  S  L  K  G  G  L  R  V  T  E  Q  G  E  M  I  R  F  K tatggtctgccagaaatcaccgtcagcagcctgtcgctttataccggggcgattctggaa
 Y  G  L  P  E  I  T  V  S  S  L  S  L  Y  T  G  A  I  L  E gccaacctgctgccaccgccggagccgaaagagagctggcgtcgcattatggatgaactg
 A  N  L  L  P  P  P  E  P  K  E  S  W  R  R  I  M  D  E  L tcagtcatctcctgcgatgtctaccgcggctacgtacgtgaaaacaaagattttgtgcct
 S  V  I  S  C  D  V  Y  R  G  Y  V  R  E  N  K  D  F  V  P tacttccgctccgctacgccggaacaagaactgggcaaactgccgttgggttcacgtccg
 Y  F  R  S  A  T  P  E  Q  E  L  G  K  L  P  L  G  S  R  P gcgaaacgtcgcccaaccggcggcgtcgagtcactacgcgccattccgtggatcttcgcc
 A  K  R  R  P  T  G  G  V  E  S  L  R  A  I  P  W  I  F  A tggacgcaaaaccgtctgatgctccccgcctggctgggtgcaggtacggcgctgcaaaaa
 W  T  Q  N  R  L  M  L  P  A  W  L  G  A  G  T  A  L  Q  K gtggtcgaagacggcaaacagagcgagctggaggctatgtgccgcgattggccattcttc
 V  V  E  D  G  K  Q  S  E  L  E  A  M  C  R  D  W  P  F  F tcgacgcgtctcggcatgctggagatggtcttcgccaaagcagacctgtggctggcggaa
 S  T  R  L  G  M  L  E  M  V  F  A  K  A  D  L  W  L  A  E tactatgaccaacgcctggtagacaaagcactgtggccgttaggtaaagagttacgcaac
 Y  Y  D  Q  R  L  V  D  K  A  L  W  P  L  G  K  E  L  R  N ctgcaagaagaagacatcaaagtggtgctggcgattgccaacgattcccatctgatggcc
 L  Q  E  E  D  I  K  V  V  L  A  I  A  N  D  S  H  L  M  A gatctgccgtggattgcagagtctattcagctacggaatatttacaccgacccgctgaac
 D  L  P  W  I  A  E  S  I  Q  L  R  N  I  Y  T  D  P  L  N gtattgcaggccgagttgctgcaccgctcccgccaggcagaaaaagaaggccaggaaccg
 V  L  Q  A  E  L  L  H  R  S  R  Q  A  E  K  E  G  Q  E  P gatcctcgcgtcgaacaagcgttaatggtcactattgccgggattgcggcaggtatgcgt
 D  P  R  V  E  Q  A  L  M  V  T  I  A  G  I  A  A  G  M  R aataccggctaa
 N  T  G  -

E. coli Citrate Synthase
atggctgatacaaaagcaaaactcaccctcaacggggatacagctgttgaactggatgtg    (SEQ ID NO: 7)
 M  A  D  T  K  A  K  L  T  L  N  G  D  T  A  V  E  L  D  V    (SEQ ID NO: 8)

ctgaaaggcacgctgggtcaagatgttattgatatccgtactctcggttcaaaaggtgtg
 L  K  G  T  L  G  Q  D  V  I  D  I  R  T  L  G  S  K  G  V ttacctttgacccaggcttcacttcaaccgcatcctgcgaatctaaaattactttttatt
 F  T  F  D  P  G  F  T  S  T  A  S  C  E  S  K  I  T  F  I gatggtgatgaaggtattttgctgcaccgcggtttcccgatcgatcagctggcgaccgat
 D  G  D  E  G  I  L  L  H  R  G  F  P  I  D  Q  L  A  T  D tctaactacctggaagtttgttacatcctgctgaatggtgaaaaaccgactcaggaacag
 S  N  Y  L  E  V  C  Y  I  L  L  N  G  E  K  P  T  Q  E  Q tatgacgaatttaaaactacggtgacccgtcataccatgatccacgagcagattacccgt
 Y  D  E  F  K  T  T  V  T  R  H  T  M  I  H  E  Q  I  T  R ctgttccatgctttccgtcgcgactcgcatccaatggcagtcatgtgtggtattaccggc
 L  F  H  A  F  R  R  D  S  H  P  M  A  V  M  C  G  I  T  G gcgctggcggcgttctatcacgactcgctggatgttaacaatcctcgtcaccgtgaaatt
 A  L  A  A  F  Y  H  D  S  L  D  V  N  N  P  R  H  R  E  I gccgcgttccgcctgctgtcgaaaatgccgaccatggccgcgatgtgttacaagtattcc
 A  A  F  R  L  L  S  K  M  P  T  M  A  A  M  C  Y  K  Y  S
```

```
attggtcagccatttgtttacccgcgcaacgatctctcctacgccgtaacttcctgaat
 I  G  Q  P  F  V  Y  P  R  N  D  L  S  Y  A  G  N  F  L  N atgatgttctccacgccgtgcgaaccgtatgaagttaatccgattctggaacgtgctatg
 M  M  F  S  T  P  C  E  P  Y  E  V  N  P  I  L  E  R  A  M gaccgtattctgatcctgcacgctgaccatgaacagaacgcctctacctccaccgtgcgt
 D  R  I  L  I  L  H  A  D  H  E  Q  N  A  S  T  S  T  V  R accgctggctcttcgggtgcgaacccgtttgcctgtatcgcagcaggtattgcttcactg
 T  A  G  S  S  G  A  N  P  F  A  C  I  A  A  G  I  A  S  L tggggacctgcgcacggcggtgctaacgaagcggcgctgaaaatgctggaagaaatcagc
 W  G  P  A  H  G  G  A  N  E  A  A  L  K  M  L  E  E  I  S tccgttaaacacattccggaatttgttcgtcgtgcgaaagacaaaaatgattctttccgc
 S  V  K  H  I  P  E  F  V  R  R  A  K  D  K  N  D  S  F  R ctgatgggcttcggtcaccgcgtgtacaaaaattacgacccgcgcgccaccgtaatgcgt
 L  M  G  F  G  H  R  V  Y  K  N  Y  D  P  R  A  T  V  M  R gaaacctgccatgaagtgctgaaagagctgggcacgaaggatgacctgctggaagtggct
 E  T  C  H  E  V  L  K  E  L  G  T  K  D  D  L  L  E  V  A atggagctggaaaacatcgcgctgaacgacccgtactttatcgagaagaaactgtaccog
 M  E  L  E  N  I  A  L  N  D  P  Y  F  I  E  K  K  L  Y  P aacgtcgatttctactctggtatcatcctgaaagcgatgggtattccgtcttccatgttc
 N  V  D  F  Y  S  G  I  I  L  K  A  M  G  I  P  S  S  M  F accgtcattttcgcaatggcacgtaccgttggctggatcgcccactggagcgaaatgcac
 T  V  I  F  A  M  A  R  T  V  G  W  I  A  H  W  S  E  M  H agtgacggtatgaagattgcccgtccgcgtcagctgtatacaggatatgaaaaacgcgac
 S  D  G  M  K  I  A  R  P  R  Q  L  Y  T  G  Y  E  K  R  D Tttaaaagcgatatcaagcgttaa
 F  K  S  D  I  K  R  -

E. coli Aconitase A
atgtcgtcaaccctacgagaagccagtaaggacacgttgcaggccaaagataaaacttac    (SEQ ID NO: 9)
 M  S  S  T  L  R  E  A  S  K  D  T  L  Q  A  K  D  K  T  Y     (SEQ ID NO: 10)

cactactacagcctgccgcttgctgctaaatcactgggcgatatcacccgtctacccaag
 H  Y  Y  S  L  P  L  A  A  K  S  L  G  D  I  T  R  L  P  K tcactcaaagttttgctcgaaaacctgctgcgctggcaggatggtaactcggttaccgaa
 S  L  K  V  L  L  E  N  L  L  R  W  Q  D  G  N  S  V  T  E gaggatatccacgcgctggcaggatggctgaaaaatgcccatgctgaccgtgaaattgcc
 E  D  I  H  A  L  A  G  W  L  K  N  A  H  A  D  R  E  I  A taccgcccggcaagggtgctgatgcaggactttaccggcgtacctgccgttgttgatctg
 Y  R  P  A  R  V  L  M  Q  D  F  T  G  V  P  A  V  V  D  L gcggcaatgcgcgaagcggttaaacgcctcggcggcgatactgcaaaggttaacccgctc
 A  A  M  R  E  A  V  K  R  L  G  G  D  T  A  K  V  N  P  L tcaccggtcgacctggtcattgaccactcggtgaccgtcgatcgttttggtgatgatgag
 S  P  V  D  L  V  I  D  H  S  V  T  V  D  R  F  G  D  D  E gcatttgaagaaaacgtacgcctggaaatggagcgcaaccacgaacgttatgtgttcctg
 A  F  E  E  N  V  R  L  E  M  E  R  N  H  E  R  Y  V  F  L aaatggggaaagcaagcgttcagtcggtttagcgtcgtgccgccaggcacaggcatttgc
 K  W  G  K  Q  A  F  S  R  F  S  V  V  P  P  G  T  G  I  C catcaggttaacctcgaatatctcggcaaagcagtgtgggagtgaattgcaggacggtgaa
 H  Q  V  N  L  E  Y  L  G  K  A  V  W  S  E  L  Q  D  G  E tggattgcttatccggatacactcgttggtactgactcgcacaccaccatgatcaacggc
 W  I  A  Y  P  D  T  L  V  G  T  D  S  H  T  T  M  I  N  G cttggcgtgctggggtggggcgttggtgggatcgaagcagaagccgcaatgttaggccag
 L  G  V  L  G  W  G  V  G  G  I  E  A  E  A  A  M  L  G  Q ccggtttccatgcttatcccggatgtagtgggcttcaaacttaccggaaaattacgtgaa
 P  V  S  M  L  I  P  D  V  V  G  F  K  L  T  G  K  L  R  E
```

```
ggtattaccgccacagacctggttctcactgttacccaaatgctgcgcaaacatggcgtg
 G  I  T  A  T  D  L  V  L  T  V  T  Q  M  L  R  K  H  G  V gtggggaaattcgtcgaattttatggtgatggtctggattcactaccgttggcggatcgc
 V  G  K  F  V  E  F  Y  G  D  G  L  D  S  L  P  L  A  D  R gccaccattgccaatatgtcgccagaatatggtgccacctgtggcttcttcccaatcgat
 A  T  I  A  N  M  S  P  E  Y  G  A  T  C  G  F  F  P  I  D gctgtaaccctcgattacatgcgtttaagcgggcgcagcgaagatcaggtcgagttggtc
 A  V  T  L  D  Y  M  R  L  S  G  R  S  E  D  Q  V  E  L  V gaaaaatatgccaaagcgcagggcatgtggcgtaacccgggcgatgaaccaattttacc
 E  K  Y  A  K  A  Q  G  M  W  R  N  P  G  D  E  P  I  F  T agtacgttagaactggatatgaatgacgttgaagcgagcctggcagggcctaaacgccca
 S  T  L  E  L  D  M  N  D  V  E  A  S  L  A  G  P  K  R  P caggatcgcgttgcactgcccgatgtaccaaaagcatttgccgccagtaacgaactggaa
 Q  D  R  V  A  L  P  D  V  P  K  A  F  A  A  S  N  E  L  E gtgaatgccacgcataaagatcgccagccggtcgattatgttatgaacggacatcagtat
 V  N  A  T  H  K  D  R  Q  P  V  D  Y  V  M  N  G  H  Q  Y cagttacctgatggcgctgtggtcattgctgcgataacctcgtgcaccaacacctctaac
 Q  L  P  D  G  A  V  V  I  A  A  I  T  S  C  T  N  T  S  N ccaagtgtgctgatggccgcaggcttgctggcgaaaaaagccgtaactctgggcctcaag
 P  S  V  L  M  A  A  G  L  L  A  K  K  A  V  T  L  G  L  K cggcaaccatgggtcaaagcgtcgctggcaccgggttcgaaagtcgtttctgattatctg
 R  Q  P  W  V  K  A  S  L  A  P  G  S  K  V  V  S  D  Y  L gcaaaagcgaaactgacaccgtatctcgacgaactgggggtttaaccttgtgggatacggt
 A  K  A  K  L  T  P  Y  L  D  E  L  G  F  N  L  V  G  Y  G tgtaccacctgtattggtaactctgggccgctgcccgatcctatcgaaacggcaatcaaa
 C  T  T  C  I  G  N  S  G  P  L  P  D  P  I  E  T  A  I  K aaaagcgatttaaccgtcggtgcggtgctgtccggcaaccgtaactttgaaggccgtatc
 K  S  D  L  T  V  G  A  V  L  S  G  N  R  N  F  E  G  R  I catccgctggttaaaactaactggctggcctcgccgccgctggtggttgcctatgcgctg
 H  P  L  V  K  T  N  W  L  A  S  P  P  L  V  V  A  Y  A  L gcgggaaatatgaatatcaacctggcttctgagcctatcggccatgatcgcaaaggcgat
 A  G  N  M  N  I  N  L  A  S  E  P  I  G  H  D  R  K  G  D ccggtttatctgaaagatatctggccatcggcacaagaaattgcccgtgcggtagaacaa
 P  V  Y  L  K  D  I  W  P  S  A  Q  E  I  A  R  A  V  E  Q gtctccacagaaatgttccgcaaagagtacgcagaagttttttgaaggcacagcagagtgg
 V  S  T  E  M  F  R  K  E  Y  A  E  V  F  E  G  T  A  E  W aagggaattaacgtcacacgatccgatacctacggttggcaggaggactcaacctatatt
 K  G  I  N  V  T  R  S  D  T  Y  G  W  Q  E  D  S  T  Y  I cgcttatcgcctttctttgatgaaatgcaggcaacaccagcaccagtggaagatattcac
 R  L  S  P  F  F  D  E  M  Q  A  T  P  A  P  V  E  D  I  H ggtgcgcggatcctcgcaatgctggggggattcagtcaccactgaccatatctctccggcg
 G  A  R  I  L  A  M  L  G  D  S  V  T  T  D  H  I  S  P  A ggcagtattaagcccgacagcccagcgggtcgatatctacaaggtcggggtgttgagcga
 G  S  I  K  P  D  S  P  A  G  R  Y  L  Q  G  R  G  V  E  R aaagactttaactcctacggttcgcggcgtggtaaccatgaagtgatgatgcgcggcacc
 K  D  F  N  S  Y  G  S  R  R  G  N  H  E  V  M  M  R  G  T ttcgccaatattcgcatccgtaatgaaatggtgcctggcgttgaagggggatgacgcgg
 F  A  N  I  R  I  R  N  E  M  V  P  G  V  E  G  G  M  T  R catttacctgacagcgacgtagtctctatttatgatgctgcgatgcgctataagcaggag
 H  L  P  D  S  D  V  V  S  I  Y  D  A  A  M  R  Y  K  Q  E caaacgccgctggcggtgattgccgggaaagagtatggatcaggctccagtcgtgactgg
 Q  T  P  L  A  V  I  A  G  K  E  Y  G  S  G  S  S  R  D  W gcggcaaaaggtccgcgtctgcttggtattcgtgtggtgattgccgaatcgtttgaacga
 A  A  K  G  P  R  L  L  G  I  R  V  V  I  A  E  S  F  E  R
```

```
attcaccgttcgaatttaattggcatgggcatcctgccgctggaatttccgcaaggcgta
 I  H  R  S  N  L  I  G  M  G  I  L  P  L  E  F  P  Q  G  V acgcgtaaaacgttagggctaaccggggaagagaagattgatattggcgatctgcaaaac
 T  R  K  T  L  G  L  T  G  E  E  K  I  D  I  G  D  L  Q  N ctacaacccggcgacggttccggtgacgcttacgcgcgcggatggtagccaggaagtc
 L  Q  P  G  A  T  V  P  V  T  L  T  R  A  D  G  S  Q  E  V gtaccctgccgttgtcgtatcgacaccgcgacggagttgacctactaccagaacgacggc
 V  P  C  R  R  I  D  T  A  T  E  L  T  Y  Y  Q  N  D  G
Attttgcattatgtcattcgtaatatgttgaagtaa
 I  L  H  Y  V  I  R  N  M  L  K  -
```

E. coli Aconitase B
```
atgctagaagaataccgtaagcacgtagctgagcgtgccgctgaggggattgcgcccaaa      (SEQ ID NO: 11)
 M  L  E  E  Y  R  K  H  V  A  E  R  A  A  E  G  I  A  P  K       (SEQ ID NO: 12)

cccctggatgcaaaccaaatggccgcacttgtagagctgctgaaaaacccgcccgcgggc
 P  L  D  A  N  Q  M  A  A  L  V  E  L  L  K  N  P  P  A  G gaagaagaattcctgttagatctgttaaccaaccgtgttcccccaggcgtcgatgaagcc
 E  E  E  F  L  L  D  L  L  T  N  R  V  P  P  G  V  D  E  A gcctatgtcaaagcaggcttcctggctgctatcgcgaaaggcgaagccaatcccctctg
 A  Y  V  K  A  G  F  L  A  A  I  A  K  G  E  A  K  S  P  L ctgactccggaaaaagccatcgaactgctgggcaccatgcagggtggttacaacattcat
 L  T  P  E  K  A  I  E  L  L  G  T  M  Q  G  G  Y  N  I  H ccgctgatcgacgcgctggatgatgccaaactggcacctattgctgccaaagcactttct
 P  L  I  D  A  L  D  D  A  K  L  A  P  I  A  A  K  A  L  S cacacgctgctgatgttcgataacttctatgacgtagaagagaaagcgaaagcaggcaac
 H  T  L  L  M  F  D  N  F  Y  D  V  E  E  K  A  K  A  G  N gaatatgcgaagcaggttatgcagtcctgggcggatgccgaatggttcctgaatcgcccg
 E  Y  A  K  Q  V  M  Q  S  W  A  D  A  E  W  F  L  N  R  P gcgctggctgaaaaactgaccgttactgtcttcaaagtcactggcgaaactaacaccgat
 A  L  A  E  K  L  T  V  T  V  F  K  V  T  G  E  T  N  T  D gacctttctccggcaccggatgcgtggtcacgcccggatatccccactgcacgcgctggcg
 D  L  S  P  A  P  D  A  W  S  R  P  D  I  P  L  H  A  L  A atgctgaaaaacgcccgtgaaggtattgagccagaccagcctggtgttgttggtccgatc
 M  L  K  N  A  R  E  G  I  E  P  D  Q  P  G  V  V  G  P  I aagcaaatcgaagctctgcaacagaaaggtttcccgctggcgtacgtcggtgacgttgtg
 K  Q  I  E  A  L  Q  Q  K  G  F  P  L  A  Y  V  G  D  V  V ggtacgggttcttcgcgtaaatccgccactaactccgttctgtggtttatgggcgatgat
 G  T  G  S  S  R  K  S  A  T  N  S  V  L  W  F  M  G  D  D attccacatgtgccgaacaaacgcggcggtggtttgtgcctcggcggtaaaattgcaccc
 I  P  H  V  P  N  K  R  G  G  G  L  C  L  G  G  K  I  A  P atcttctttaacacgatggaagacgcgggtgcactgccaatcgaagtcgacgtctctaac
 I  F  F  N  T  M  E  D  A  G  A  L  P  I  E  V  D  V  S  N ctgaacatgggcgacgtgattgacgtttacccgtacaaaggtgaagtgcgtaaccacgaa
 L  N  M  G  D  V  I  D  V  Y  P  Y  K  G  E  V  R  N  H  E accggcgaactgctggcgaccttcgaactgaaaaccgacgtgctgattgatgaagtgcgt
 T  G  E  L  L  A  T  F  E  L  K  T  D  V  L  I  D  E  V  R gctggtggccgtattccgctgattatcggcgtggcctgaccaccaaagcgcgtgaagca
 A  G  G  R  I  P  L  I  I  G  R  G  L  T  T  K  A  R  E  A cttggtctgccgcacagtgatgtgttccgtcaggcgaaagatgtcgctgagagcgatcgc
 L  G  L  P  H  S  D  V  F  R  Q  A  K  D  V  A  E  S  D  R ggcttctcgctggcgcaaaaaatggtaggccgtgcctgtggcgtgaaaggcattcgtccg
 G  F  S  L  A  Q  K  M  V  G  R  A  C  G  V  K  G  I  R  P ggcgcgtactgtgaaccgaaaatgacttctgtaggttcccaggacaccaccggcccgatg
 G  A  Y  C  E  P  K  M  T  S  V  G  S  Q  D  T  T  G  P  M acccgtgatgaactgaaagacctggcgtgcctgggcttctcggctgacctggtgatgcag
 T  R  D  E  L  K  D  L  A  C  L  G  F  S  A  D  L  V  M  Q
```

-continued

```
tctttctgccacaccgcggcgtatccgaagccagttgacgtgaacacgcaccacacgctg
 S   F   C   H   T   A   A   Y   P   K   P   V   D   V   N   T   H   H   T   L ccggacttcattatgaaccgtggcggtgtgtcgctgcgtccgggtgacggcgtcattcac
 P   D   F   I   M   N   R   G   G   V   S   L   R   P   G   D   G   V   I   H tcctggctgaaccgtatgctgctgccggataccgtcggtaccggtggtgactcccatacc
 S   W   L   N   R   M   L   L   P   D   T   V   G   T   G   G   D   S   H   T cgtttcccgatcggtatctctttcccggcgggttctggtctggtggcgtttgctgccgca
 R   F   P   I   G   I   S   F   P   A   G   S   G   L   V   A   F   A   A   A actggcgtaatgccgcttgatatgccggaatccgttctggtgcgcttcaaaggcaaaatg
 T   G   V   M   P   L   D   M   P   E   S   V   L   V   R   F   K   G   K   M cagccgggcatcaccctgcgcgatctggtacacgctattccgctgtatgcgatcaaacaa
 Q   P   G   I   T   L   R   D   L   V   H   A   I   P   L   Y   A   I   K   Q ggtctgctgaccgttgagaagaaaggcaagaaaaacatcttctctggccgcatcctggaa
 G   L   L   T   V   E   K   K   G   K   K   N   I   F   S   G   R   I   L   E attgaaggtctgccggatctgaaagttgagcaggcctttgagctaaccgatgcgtccgcc
 I   E   G   L   P   D   L   K   V   E   Q   A   F   E   L   T   D   A   S   A gagcgttctgccgctggttgtaccatcaagctgaacaaagaaccgatcatcgaatacctg
 E   R   S   A   A   G   C   T   I   K   L   N   K   E   P   I   I   E   Y   L aactctaacatcgtcctgctgaagtggatgatcgcggaaggttacggcgatcgtcgtacc
 N   S   N   I   V   L   L   K   W   M   I   A   E   G   Y   G   D   R   R   T ctggaacgtcgtattcagggcatggaaaaatggctggcgaatcctgagctgctggaagcc
 L   E   R   R   I   Q   G   M   E   K   W   L   A   N   P   E   L   L   E   A gatgcagatgcggaatacgcggcagtgatcgacatcgatctggcggatattaaagagcca
 D   A   D   A   E   Y   A   A   V   I   D   I   D   L   A   D   I   K   E   P atcctgtgtgctccgaacgacccggatgacgcgcgtccgctgtctgcggtacagggtgag
 I   L   C   A   P   N   D   P   D   D   A   R   P   L   S   A   V   Q   G   E aagatcgacgaagtgtttatcggttcctgcatgaccaacatcggtcacttccgtgctgcg
 K   I   D   E   V   F   I   G   S   C   M   T   N   I   G   H   F   R   A   A ggtaaactgctggatgcgcataaaggtcagttgccgacccgcctgtgggtggcaccgcca
 G   K   L   L   D   A   H   K   G   Q   L   P   T   R   L   W   V   A   P   P acccgtatggacgccgcacagttgaccgaagaaggctactacagcgtcttcggtaagagt
 T   R   M   D   A   A   Q   L   T   E   E   G   Y   Y   S   V   F   G   K   S ggtgcgcgtatcgagatccctggctgttccctgtgtatgggtaaccaggcgcgtgtggcg
 G   A   R   I   E   I   P   G   C   S   L   C   M   G   N   Q   A   R   V   A gacggtgcaacggtggtttccacctctacccgtaacttcccgaaccgtctgggtactggc
 D   G   A   T   V   V   S   T   S   T   R   N   F   P   N   R   L   G   T   G gcgaatgtcttcctggcttctgcggaactggcggctgttgcggcgctgattggcaaactg
 A   N   V   F   L   A   S   A   E   L   A   A   V   A   A   L   I   G   K   L ccgacgccggaagagtaccagacctacgtggcgcaggtagataaaacagccgttgatact
 P   T   P   E   E   Y   Q   T   Y   V   A   Q   V   D   K   T   A   V   D   T taccgttatctgaacttcaaccagctttctcagtacaccgagaaagccgatggggtgatt
 Y   R   Y   L   N   F   N   Q   L   S   Q   Y   T   E   K   A   D   G   V   I ttccagactgcggtttaa
 F   Q   T   A   V   -
```

Table 1 below lists additional examples of phosphoenolpyruvate carboxylases/carboxykinase, citrate synthases, and aconitases, as well as exemplary 2-methylcitrate synthases, citrate lyases, and 2-methylcitrate dehydratase:

TABLE 1

Enzymes Involved in Itaconic Acid Synthesis

| Enzymes | GenBank Accession Numbers |
|---|---|
| Phosphoenolpyruvate carboxykinase/carboxylase | NP_417862 (*E. coli*, EC4.1.1.49); AAB07805 (*S. aureus*, EC4.1.1.32); CAC32156 (*M. leprae*), XP_645396 (*D. discoideum*); EDN6000 (*S. cerevisiae*); and XP_001210573 (*A. terreus*); PC2168 (*E. coli*, EC4.1.1.38), NP_850372 (*A. thaliana*); CAA35251 (*S. bicolor*); CAB95920 (*S. coelicolor*); XP_001391222 (*A. niger*) |
| Citrate synthase | AAC73814 (*E. coli*); NP_001080194 (*X. laevis*); CAB66275 (*S. coelicolor*); NP_080720 (*M. musculus*); ABP36423 (*C. phaeovibrioides*); XP_001827205 (*A. oryzae*); and EDN 61138 (*S. cerevisiae*) |
| 2-methylcitrate synthase | ABN63514 (*S. baltica*); ABI57944 (*A. ehrlichei*); AP_000985 (*E. coli*); XP_001209805 (*A. terreus*); P45858 (*B. subtilis*); Q56063 (*S. typhimurium*) |
| Citrate lyase | YP_662283 (*P. atlantica*); ABH11558 (*L. helveticus*); AAL50820 (*R. erythropolis*); AP_001263 (*E. coli*); XP_750953 (*A. fumigatus*); and NP_669690 (*Y. pestis*) |
| Aconitase | CAA90177 (*B. taurus*); CAQ017353 (*C. michiganesis*); CAC37548 (*S. coelicolor*); AAC46192 (*M. avium*); 1L5JB (*E. coli*); EDN59216 (*S. cerevisiae*); AAC61778 (*A. terreus*); YP_910600 (*C. phaeobacteroides*) |
| 2-methylcitrate dehydratase | ZP_03698315 (*L. nitroferrum*); YP_002029406 (*S. maltophilia*); AP_000986 (*E. coli*); EDV11211 (*S. cerevisiae*); XP_001209777 (*A. terreus*); YP_001860514 (*B. phymatum*) |

The above-described genetically modified microorganisms can be constructed by conventional recombinant technology (see, e.g., Sambrook et al., Molecular Cloning: A Laboratory Manual, Cold Spring Harbor Laboratory Press.)

More specifically, a microorganism strain that overly expresses one or more of the enzymes mentioned above can be obtained as follows. A DNA fragment(s) encoding the one or more of the enzymes mentioned above can be obtained by polymerase chain reaction from its natural source(s) based on its coding sequence(s), which can be retrieved from GenBank. The DNA fragment(s) is then operably linked to a suitable promoter to produce an expression cassette. In one example, one expression cassette includes one coding sequence operably linked to a promoter. In another example, one expression cassette includes multiple coding sequences, all of which are in operative linkage with a promoter. In that case, it is preferred that a ribosomal binding site is incorporated 5' to each of the coding sequences. If desired, the coding sequences are subjected to codon optimization based on the optimal codon usage in the host microorganism.

As used herein, the term "promoter" refers to a nucleotide sequence containing elements that initiate the transcription of an operably linked nucleic acid sequence in a desired host microorganism. At a minimum, a promoter contains an RNA polymerase binding site. It can further contain one or more enhancer elements which, by definition, enhance transcription, or one or more regulatory elements that control the on/off status of the promoter. When *E. coli* is used as the host microorganism, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al., *Gene* 20:231-243, 1982). When yeast is used as the host microorganism, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of microorganisms are also well known in the art.

The expression cassette(s) described above is then introduced into a suitable microorganism to produce the genetically modified microorganisms disclosed herein. Positive transformants are selected and the over-expression of one or more of the enzymes mentioned above are confirmed by methods known in the art, e.g., immune-blotting or enzymatic activity analysis. The modified microorganisms are then cultured in a suitable medium for itaconic acid production. Preferably, the medium contains glucose or citrate as the precursor for making itaconic acid. After a sufficient culturing period, the medium is collected and the secreted itaconic acid is isolated.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Plasmids and Genetically Modified *E. coli* Strains

*E. coli* strains BW25113 (rrnB$_{T14}$ ΔlacZ$_{WJ16}$ hsdR514 ΔaraBAD$_{AH33}$ ΔrhaBAD$_{LD78}$) and BL21 (dcm ompT hsdS (r$_B$-m$_B$-) gal), used as the parent strains (see Datsehko et al., Proc. Natl. Acad. Sci. USA, 97:6640-6645, 2000), were genetically modified by recombinant technology. Briefly, the endogenous icd gene in BW25113 was disrupted by FLP-FRT recombination to produce a BW25113 mutant (i.e., PCI400), which expressed a lower level of isocitrate dehydrogenase as compared to BW25113.

A number of expression plasmids to be introduced into the parent strains and PCI400, shown in Table 2 below, were constructed by recombinant technology.

TABLE 2

Expression Plasmids

| Plasmid Name | Genotype |
|---|---|
| pZE12-luc | ColE1 ori; Amp$^R$; P$_L$lacO$_1$::luc(VF) |
| pPC1 | ColE1 ori; Kan$^R$; P$_L$lacO$_1$::cad(AT) |
| pPC2 | from pZE12, P$_L$lacO$_1$::acnA(EC) |
| pPC3 | from pZE12, P$_L$lacO$_1$::acnB(EC) |
| pPC4 | ColE1 ori; Spe$^R$; P$_L$lacO$_1$::gltA(EC) |
| pPC5 | ColE1 ori; Spe$^R$; P$_L$lacO$_1$::ppc(EC) |
| pPC6 | ColE1 ori; Spe$^R$; P$_L$lacO$_1$::ppc(EC)-gltA(EC) |

* luc (VF): *V. fischeri* luciferase
* Cad (AT): *A. terreus* CAD gene
* acnA(EC): *E. coli* aconitase A gene
* acnB(EC): *E. coli* aconitase B gene
* gltA (EC): *E. coli* citrate synthase gene
* ppc (EC): *E. coli* phosphoenolpyruvate carboxylase gene One or more of the plasmids listed in Table 2 above were introduced into BW25113, PCI400, or BL21 to produce various modified *E. coli* strains, which are listed in Table 3 below:

TABLE 3

Genetically Modified E. coli Strains

| Names | Parent strain | Plasmid(s) introduced |
|---|---|---|
| PCI 010 | BW25133 | pPC1 |
| PCI 011 | BW25133 | pPC1 and pPC5 |
| PCI 012 | BW25133 | pPC1 and pPC4 |
| PCI 013 | BW25133 | pPC1 and pPC3 |
| PCI 014 | BW25133 | pPC1, pPC3, and pPC5 |
| PCI 015 | BW25133 | pPC1, pPC3, and pPC4 |
| PCI 016 | BW25133 | pPC1, pPC3, and pPC6 |
| PCI 017 | BW25133 | pPC1 and pPC6 |
| PCI 019 | BW25133 | pPC1, pPC2, and pPC6 |
| PCI 213 | BL21 | pPC1 |
| PCI 510 | PCI400 | pPC1 |
| PCI 511 | PCI400 | pPC1 and pPC5 |
| PCI 512 | PCI400 | pPC1 and pPC4 |
| PCI 513 | PCI400 | pPC1 and pPC3 |
| PCI 514 | PCI400 | pPC1, pPC3, and pPC5 |
| PCI 515 | PCI400 | pPC1, pPC3, and pPC4 |
| PCI 516 | PCI400 | pPC1, pPC3, and pPC6 |
| PCI 517 | PCI400 | pPC1 and pPC6 |
| PCI 519 | PCI400 | pPC1, pPC2, and pPC6 |

EXAMPLE 2

Producing Itaconic Acid in PCI213

Strain PCI 213 (BL21 over-expressing *A. terreus* CAD) was cultured overnight at 37° C. in Luria-Bertani (LB) medium. The overnight culture was inoculated (1%) into a minimal medium containing 80 g/L glucose, sodium chloride, and sodium phosphate buffer and cultured at 30° C. for a suitable period until the optical density at 600 nm ($OD_{600}$) reached 0.2-0.6. Isopropyl β-D-1-thiogalactopyranoside (IPTG) was then added to the culture (0.5 mM) to induce expression of CAD. 24 hours later, the culture medium was collected. The itaconic acid concentration in the medium was about 100 mg/L.

EXAMPLE 3

Producing Itaconic Acid in PCI010

Strain PCI 010 (BW25133 over-expressing *A. terreus* CAD) was cultured overnight at 37° C. in a minimal medium containing 40 g/L glucose, sodium chloride, and sodium phosphate buffer. The overnight culture was inoculated into M9 medium containing 20 or 40 g/L glucose, sodium chloride, and sodium phosphate buffer, supplemented with or without 1 mM glutamate, and cultured at 30° C. 0.5 mM IPTG was added to the culture when its $OD_{600}$ reached 0.2~0.4 to induce expression of *A. terreus* CAD. The culture medium was collected 24 hours later and the amount of itaconic acid was determined. The results obtained from this study were shown in Table 4 below.

TABLE 4

Itaconic Acid Production in PCI010

| Ingredients in minimal medium | | Itaconic Acid |
|---|---|---|
| glucose (g/L) | glutamate (1 mM) | (mg/L) |
| 20 | − | 168.86 |
| 40 | − | 163.27 |
| 20 | + | 57.05 |
| 40 | + | 88.85 |

EXAMPLE 4

Production of Itaconic Acid in Various Modified *E. coli* Strains Using Glucose as Substrate The modified *E. coli* strains listed in Table 5 below were cultured in LB medium overnight at 37° C. in a rotary shaker (250 rpm). The overnight cultures were inoculated into M9 medium containing 20 g/L glucose, 1 g/L yeast extract, sodium chloride, and sodium phosphate buffer, and cultured at 37° C. 0.5 mM IPTG was added to each of the cultures when their $OD_{600}$ reached 0.2~0.4 to induce exogenous gene expression. The culture media were collected at different time points shown in Table 5 below and the amounts of itaconic acid contained therein were determined.

TABLE 5

Production of Itaconic Acid in Genetically Modified *E. coli* Strains

| *E. coli* Strain | Itaconate production (g/L) | Culture Time (h) |
|---|---|---|
| PCI 014 | 0.005 | 48 |
| PCI 013 | 0.021 | 48 |
| PCI 015 | 0.032 | 48 |
| PCI 016 | 0.034 | 48 |
| PCI 010 | 0.054 | 48 |
| PCI 010 | 0.057 | 70 |
| PCI 514 | 0.074 | 49 |
| PCI 510 | 0.280 | 49 |
| PCI 511 | 0.288 | 49 |
| PCI 513 | 0.346 | 49 |
| PCI 512 | 0.404 | 49 |
| PCI 515 | 0.598 | 49 |
| PCI 516 | 2.106 | 49 |
| PCI 516 | 4.02 | 72 |
| PCI 519 | 4.158 | 73 |

As shown in Table 5 above, both strains PCI 519 (BW25133; Δicd, gltA, ppc, cad and acnA) and PCI 516 (BW25133; Δicd, gltA, ppc, cad and acnB) produced more than 4 g/L itaconic acid in the medium after being cultured for 72-hours. The glucose-to-itaconic acid conversion rates of PCI 519 and PCI 516 were about 0.52 g itaconic acid per gram of glucose and about 0.68 g itaconic acid per gram of glucose.

EXAMPLE 5

Producing Itaconic Acid in Genetically Modified *E. coli* Strains Using Citrate as Substrate Strains PCI 513 (BW25133; Δicd, cad, and acnB), PCI 516, and PCI 519 were cultured in LB medium at 37° C. for about 16 hours. The *E. coli* cells were then cultured in fresh LB medium supplemented with 0.5 mM IPTG for 16 hours. The cells were then permeabilized by Triton X-100 and re-suspended in a phosphate buffer containing citrate (50 g/ml). After 48 or 72 hours, the phosphate buffer was examined for the amount of itaconic acid in it.

PCI 513 produced 1.27 g/L of itaconic acid after being cultured for 48 hours. In addition, this strain converted citrate to itaconic acid at a rate of 0.24 g itaconic acid per gram of citrate.

PCI 519 and PCI 516 produced more than 6 g/L and more than 5 g/L itaconic acid after being cultured for 70 hours. The citrate-to-itaconic acid conversion rates were 0.61 itaconic acid per gram of citrate and 0.34 g itaconic acid per gram citrate, respectively.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A genetically modified microorganism, comprising
a first exogenous nucleotide sequence encoding an *A. terreus* cis-aconitic acid decarboxylase (CAD) capable of converting cis-aconitic acid to itaconic acid, the first exogenous nucleotide sequence being operably linked to an *E. coli* promoter;
a second exogenous nucleotide sequence encoding a phosphoenolpyruvate carboxylase capable of converting phosphoenolpyruvate to oxaloacetate, the second exogenous nucleotide sequence being operably linked to an *E. coli* promoter;
a third exogenous nucleotide sequence encoding a citrate synthase capable of converting oxaloacetate to citrate, the third exogenous nucleotide sequence being operably linked to an *E. coli* promoter;
a fourth exogenous nucleotide sequence encoding an aconitase capable of converting citrate or isocitrate to cis-aconitic acid, the fourth exogenous nucleotide sequence being operably linked to an *E. coli* promoter; and
a mutated endogenous icd gene disrupted by a deletion or insertion, the mutated endogenous icd gene expressing a lower level of isocitrate dehydrogenase relative to its wild-type counterpart;
wherein the genetically modified microorganism is an *E. coli* hat over-expresses the CAD, the phosphoenolpyruvate carboxylase, the citrate synthase and the aconitase as compared to its wild-type counterpart, and is capable of producing itaconic acid from glucose or citrate as a substrate.

2. A method for producing itaconic acid in a microorganism, comprising
   providing the genetically modified microorganism of claim 1,
   cultivating the genetically modified microorganism in a medium to produce itaconic acid, and
   collecting the medium for isolation of the itaconic acid thus produced.

3. The method of claim 2, wherein the medium contains glucose at a concentration of 5-80 g/L.

4. The method of claim 3, wherein the glucose concentration is 10-40 g/L.

5. The method of claim 2, wherein the genetically modified microorganism is permeablized and the medium contains citrate at a concentration of 5-80 g/L.

6. The method of claim 5, wherein the citrate concentration is 10-40 g/L.

7. The genetically modified microorganism of claim 1, wherein the first exogenous nucleotide sequence encodes the amino acid sequence of SEQ ID NO:2.

8. The genetically modified microorganism of claim 7, wherein the first exogenous nucleotide sequence comprises SEQ ID NO:1.

9. The genetically modified microorganism of claim 1, wherein the second exogenous nucleotide sequence encodes an *E. coli* phosphoenolpyruvate carboxylase.

10. The genetically modified microorganism of claim 9, wherein the second exogenous nucleotide sequence encodes the amino acid sequence of SEQ ID NO:6.

11. The genetically modified microorganism of claim 10, wherein the second exogenous nucleotide sequence comprises SEQ ID NO:5.

12. The genetically modified microorganism of claim 1, wherein the third exogenous nucleotide sequence encodes an *E. coli* citrate synthase.

13. The genetically modified microorganism of claim 12, wherein the third exogenous nucleotide sequence encodes the amino acid sequence of SEQ ID NO:8.

14. The genetically modified microorganism of claim 13, wherein the third exogenous nucleotide sequence comprises SEQ ID NO:7.

15. The genetically modified microorganism of claim 1, wherein the fourth exogenous nucleotide sequence encodes an aconitase A.

16. The genetically modified microorganism of claim 1, wherein the fourth exogenous nucleotide sequence encodes an aconitase B.

17. The genetically modified microorganism of claim 1, wherein the fourth exogenous nucleotide sequence encodes an *E. coli* aconitase A or an *E. coli* aconitase B.

18. The genetically modified microorganism of claim 17, wherein the fourth exogenous nucleotide sequence encodes the amino acid sequence of SEQ ID NO:12.

19. The genetically modified microorganism of claim 18, wherein the fourth exogenous nucleotide sequence comprises SEQ ID NO:11.

20. The genetically modified microorganism of claim 1, wherein the CAD is a naturally-occurring enzyme from *A. terreus*, and wherein the phosphoenolpyruvate carboxylase, the citrate synthase, and the aconitase are naturally-occurring enzymes from *E. coli*.

21. The genetically modified microorganism of claim 20, wherein the first exogenous nucleotide sequence encodes the amino acid sequence of SEQ ID NO:2, the second exogenous nucleotide sequence encodes the amino acid sequence of SEQ ID NO:6, the third exogenous nucleotide sequence encodes the amino acid sequence of SEQ ID NO:8, and the fourth exogenous nucleotide sequence encodes the amino acid sequence of SEQ ID NO:12.

22. The genetically modified microorganism of claim 21, the *E. coli* promoter being the $P_L lacO_1$ promoter.

* * * * *

```
                        SEQUENCE LISTING

<160> NUMBER OF SEQ ID NOS: 12

<210> SEQ ID NO 1
<211> LENGTH: 1473
<212> TYPE: DNA
<213> ORGANISM: Aspergillus terreus

<400> SEQUENCE: 1
atgaccaagc agtctgctga ttccaacgcg aagtctggtg tgacctctga gatctgtcac      60
tgggcgtcta atctcgccac tgatgatatc ccgagcgacg ttctggagcg tgcaaaatac     120
ctgatcctgg atggtatcgc gtgcgcgtgg gtaggtgctc gtgtcccatg gtctgaaaaa     180
tacgttcaag cgaccatgtc tttcgaacct ccgggtgcgt gtcgtgtcat cggttacggc     240
cagaaactgg gtccggtagc ggctgccatg acgaactctg catttattca ggcgaccgaa     300
ctcgatgact atcactctga agcgccgctg cattccgcgt ctatcgttct cccggcagtt     360
ttcgcggcga gcgaagtact ggccgaacag ggtaaaacca tctctggtat tgacgtgatt     420
ctggctgcga tcgttggttt cgagagcggt cctcgcatcg gcaaagcgat ctacggttct     480
gacctcctga caacggctg gcactgcggt gcggtatatg gcgcaccggc tggtgcgctc     540
gcaactggta agctcctggg cctcacgccg gacagcatgg aagatgcact gggtattgcc     600
tgcacgcaag catgcggcct catgtccgcg cagtatggtg gcatggttaa acgtgttcag     660
cacggtttcg cagcgcgtaa tggtctcctc ggtggcctcc tggctcacgg cggctacgag     720
gcgatgaaag gtgttctcga gcgttcttac ggtggcttcc tgaagatgtt caccaagggc     780
aacggtcgtg aaccgccgta caagaagaa gaggttgtgg ctggtctggg tagcttctgg     840
cacaccttca ccattcgtat caaactgtac gcgtgctgcg gtctcgtaca cggtcctgtt     900
gaagccattg aaaacctcca gggtcgttac ccggaactgc tcaatcgtgc taacctgtct     960
aacatccgcc acgttcacgt acaactctct accgcgagca actcccactg tggttggatc    1020
ccagaagagc gcccaatctc ttctatcgcg ggtcaaatgt ctgtcgcata tatcctcgcc    1080
gttcagctcg ttgaccaaca gtgtctgctc agccagttct ccgagtttga cgataatctg    1140
gaacgcccgg aagtgtggga cctggcacgt aaggttacca gctctcaatc tgaggagttc    1200
gaccaggacg gtaactgtct ctctgccggt cgcgtccgta ttgagttcaa cgacggctcc    1260
tccatcaccg aatccgttga gaagccgctc ggtgtaaagg aaccaatgcc aaatgaacgc    1320
atcctgcaca ataccgtac cctggcgggt tctgtaacgg acgaaagccg tgttaaggag    1380
atcgaggatc tcgtgctcgg cctggaccgt ctgaccgata ttagcccgct cctcgagctg    1440
ctgaattgtc cggttaaatc cccactggtt taa                                 1473

<210> SEQ ID NO 2
<211> LENGTH: 490
<212> TYPE: PRT
<213> ORGANISM: Aspergillus terreus

<400> SEQUENCE: 2

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
```

```
                    20                  25                  30
Asp Val Leu Glu Arg Ala Lys Tyr Leu Ile Leu Asp Gly Ile Ala Cys
            35                  40                  45

Ala Trp Val Gly Ala Arg Val Pro Trp Ser Glu Lys Tyr Val Gln Ala
50                  55                  60

Thr Met Ser Phe Glu Pro Pro Gly Ala Cys Arg Val Ile Gly Tyr Gly
65                      70                  75                  80

Gln Lys Leu Gly Pro Val Ala Ala Met Thr Asn Ser Ala Phe Ile
                    85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
            115                 120                 125

Glu Gln Gly Lys Thr Ile Ser Gly Ile Asp Val Ile Leu Ala Ala Ile
            130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
                165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
            195                 200                 205

Ser Ala Gln Tyr Gly Gly Met Val Lys Arg Val Gln His Gly Phe Ala
            210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
                245                 250                 255

Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
            290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
            340                 345                 350

Met Ser Val Ala Tyr Ile Leu Ala Val Gln Leu Val Asp Gln Gln Cys
            355                 360                 365

Leu Leu Ser Gln Phe Ser Glu Phe Asp Asp Asn Leu Glu Arg Pro Glu
            370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
            435                 440                 445
```

Ala Gly Ser Val Thr Asp Glu Ser Arg Val Lys Glu Ile Glu Asp Leu
        450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 3
<211> LENGTH: 1251
<212> TYPE: DNA
<213> ORGANISM: Escherichia coli

<400> SEQUENCE: 3

| | | | | | |
|---|---|---|---|---|---|
| atggaaagta | aagtagttgt | tccggcacaa | ggcaagaaga | tcaccctgca | aaacggcaaa | 60
| ctcaacgttc | ctgaaaatcc | gattatccct | tacattgaag | gtgatggaat | cggtgtagat | 120
| gtaaccccag | ccatgctgaa | agtggtcgac | gctgcagtcg | agaaagccta | taaggcgag  | 180
| cgtaaaatct | cctggatgga | aatttacacc | ggtgaaaaat | ccacacaggt | ttatggtcag | 240
| gacgtctggc | tgcctgctga | aactcttgat | ctgattcgtg | aatatcgcgt | tgccattaaa | 300
| ggtccgctga | ccactccggt | tggtggcggt | attcgctctc | tgaacgttgc | cctgcgccag | 360
| gaactggatc | tctacatctg | cctgcgtccg | gtacgttact | atcagggcac | tccaagcccg | 420
| gttaaacacc | tgaactgac  | cgatatggtt | atcttccgtg | aaaactcgga | agacatttat | 480
| gcgggtatcg | aatggaaagc | agactctgcc | gacgccgaga | agtgattaa  | attcctgcgt | 540
| gaagagatgg | gggtgaagaa | aattcgcttc | ccggaacatt | gtggtatcgg | tattaagccg | 600
| tgttcggaag | aaggcaccaa | acgtctggtt | cgtgcagcga | tcgaatacgc | aattgctaac | 660
| gatcgtgact | ctgtgactct | ggtgcacaaa | gcaacatca  | tgaagttcac | cgaaggagcg | 720
| tttaaagact | ggggctacca | gctggcgcgt | gaagagtttg | gcggtgaact | gatcgacggt | 780
| ggcccgtggc | tgaaagttaa | aacccgaac  | actggcaaag | atcgtcat   | taagacgtg  | 840
| attgctgatg | cattcctgca | acagatcctg | ctgcgtccgg | ctgaatatga | tgttatcgcc | 900
| tgtatgaacc | tgaacggtga | ctacatttct | gacgccctgg | cagcgcaggt | tggcggtatc | 960
| ggtatcgccc | tggtgcaaa  | catcggtgac | gaatgcgccc | tgtttgaagc | cacccacggt | 1020
| actgcgccga | atatgccgg  | tcaggacaaa | gtaaatcctg | gctctattat | tctctccgct | 1080
| gagatgatgc | tgcgccacat | gggttggacc | gaagcggctg | acttaattgt | taaggtatg  | 1140
| gaaggcgcaa | tcaacgcgaa | aaccgtaacc | tatgacttcg | agcgtctgat | ggatggcgct | 1200
| aaactgctga | atgttcaga  | gtttggtgac | gcgatcatcg | aaaacatgta | a          | 1251

<210> SEQ ID NO 4
<211> LENGTH: 416
<212> TYPE: PRT
<213> ORGANISM: Escherichia coli

<400> SEQUENCE: 4

Met Glu Ser Lys Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
            20                  25                  30

Glu Gly Asp Gly Ile Gly Val Asp Val Thr Pro Ala Met Leu Lys Val
        35                  40                  45

Val Asp Ala Ala Val Glu Lys Ala Tyr Lys Gly Glu Arg Lys Ile Ser
    50                  55                  60

Trp Met Glu Ile Tyr Thr Gly Glu Lys Ser Thr Gln Val Tyr Gly Gln

```
                65                  70                  75                  80
Asp Val Trp Leu Pro Ala Glu Thr Leu Asp Leu Ile Arg Glu Tyr Arg
                    85                  90                  95

Val Ala Ile Lys Gly Pro Leu Thr Thr Pro Val Gly Gly Ile Arg
                    100                 105                 110

Ser Leu Asn Val Ala Leu Arg Gln Glu Leu Asp Leu Tyr Ile Cys Leu
                    115                 120                 125

Arg Pro Val Arg Tyr Tyr Gln Gly Thr Pro Ser Pro Val Lys His Pro
                    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
                    165                 170                 175

Lys Phe Leu Arg Glu Glu Met Gly Val Lys Lys Ile Arg Phe Pro Glu
                    180                 185                 190

His Cys Gly Ile Gly Ile Lys Pro Cys Ser Glu Glu Gly Thr Lys Arg
                    195                 200                 205

Leu Val Arg Ala Ala Ile Glu Tyr Ala Ile Ala Asn Asp Arg Asp Ser
210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                    245                 250                 255

Leu Ile Asp Gly Gly Pro Trp Leu Lys Val Lys Asn Pro Asn Thr Gly
                    260                 265                 270

Lys Glu Ile Val Ile Lys Asp Val Ile Ala Asp Ala Phe Leu Gln Gln
                    275                 280                 285

Ile Leu Leu Arg Pro Ala Glu Tyr Asp Val Ile Ala Cys Met Asn Leu
                    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                    325                 330                 335

Ala Thr His Gly Thr Ala Pro Lys Tyr Ala Gly Gln Asp Lys Val Asn
                    340                 345                 350

Pro Gly Ser Ile Ile Leu Ser Ala Glu Met Met Leu Arg His Met Gly
                    355                 360                 365

Trp Thr Glu Ala Ala Asp Leu Ile Val Lys Gly Met Glu Gly Ala Ile
                    370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                    405                 410                 415
```

<210> SEQ ID NO 5
<211> LENGTH: 2652
<212> TYPE: DNA
<213> ORGANISM: Escherichia coli

<400> SEQUENCE: 5

```
atgaacgaac aatattccgc attgcgtagt aatgtcagta tgctcggcaa agtgctggga     60
gaaaccatca aggatgcgtt gggagaaaca attcttgaac gcgtagaaac tatccgtaag    120
ttgtcgaaat cttcacgcgc tggcaatgat gctaaccgcc aggagttgct caccaccta    180 caaaatttgt cgaacgacga gctgctgccc gttgcgcgtg cgtttagtca gttcctgaac    240
```

| | |
|---|---|
| ctggccaaca ccgccgagca ataccacagc atttcgccga aaggcgaagc tgccagcaac | 300 |
| ccggaagtga tcgcccgcac cctgcgtaaa ctgaaaaacc agccggaact gagcgaagac | 360 |
| accatcaaaa aagcagtgga atcgctgtcg ctggaactgg tcctcacggc tcacccaacc | 420 |
| gaaattaccc gtcgtacact gatccacaaa atggtggaag tgaacgcctg tttaaaacag | 480 |
| ctcgataaca aagatatcgc tgactacgaa cacaaccagc tgatgcgtcg cctgcgccag | 540 |
| ttgatcgccc agtcatggca taccgatgaa atccgtaagc tgcgtccaag cccggtagat | 600 |
| gaagccaaat ggggctttgc cgtagtggaa acagcctgt ggcaaggcgt accaaattac | 660 |
| ctgcgcgaac tgaacgaaca actggaagag aacctcggct acaaactgcc cgtcgaattt | 720 |
| gttccggtcc gttttacttc gtggatgggc ggcgaccgcg acggcaaccc gaacgtcact | 780 |
| gccgatatca cccgccacgt cctgctactc agccgctgga agccaccga tttgttcctg | 840 |
| aaagatattc aggtgctggt ttctgaactg tcgatggttg aagcgacccc tgaactgctg | 900 |
| gcgctggttg gcgaagaagg tgccgcagaa ccgtatcgct atctgatgaa aaacctgcgt | 960 |
| tctcgcctga tggcgacaca ggcatggctg gaagcgcgcc tgaaaggcga gaactgcca | 1020 |
| aaaccagaag gcctgctgac acaaaacgaa gaactgtggg aaccgctcta cgcttgctac | 1080 |
| cagtcacttc aggcgtgtgg catgggtatt atcgccaacg gcgatctgct cgacaccctg | 1140 |
| cgccgcgtga atgtttcgg cgtaccgctg gtccgtattg atatccgtca ggagagcacg | 1200 |
| cgtcataccg aagcgctggg cgagctgacc cgctacctcg gtatcggcga ctacgaaagc | 1260 |
| tggtcagagg ccgacaaaca ggcgttcctg atccgcgaac tgaactccaa acgtccgctt | 1320 |
| ctgccgcgca actggcaacc aagcgccgaa acgcgcgaag tgctcgatac ctgccaggtg | 1380 |
| attgccgaag caccgcaagg ctccattgcc gcctacgtga tctcgatggc gaaaacgccg | 1440 |
| tccgacgtac tggctgtcca cctgctgctg aaagaagcgg gtatcgggtt tgcgatgccg | 1500 |
| gttgctccgc tgtttgaaac cctcgatgat ctgaacaacg ccaacgatgt catgacccag | 1560 |
| ctgctcaata ttgactggta tcgtggcctg attcagggca acagatggt gatgattggc | 1620 |
| tattccgact cagcaaaaga tgcgggagtg atggcagctt cctgggcgca atatcaggca | 1680 |
| caggatgcat taatcaaaac ctgcgaaaaa gcgggtattg agctgacgtt gttccacggt | 1740 |
| cgcggcggtt ccattggtcg cggcggcgca cctgctcatg cggcgctgct gtcacaaccg | 1800 |
| ccaggaagcc tgaaaggcgg cctgcgcgta accgaacagg gcgagatgat ccgctttaaa | 1860 |
| tatggtctgc cagaaatcac cgtcagcagc ctgtcgcttt ataccggggc gattctggaa | 1920 |
| gccaacctgc tgccaccgcc ggagccgaaa gagagctggc gtcgcattat ggatgaactg | 1980 |
| tcagtcatct cctgcgatgt ctaccgcggc tacgtacgtg aaaacaaaga ttttgtgcct | 2040 |
| tacttccgct ccgctacgcc ggaacaagaa ctgggcaaac tgccgttggg ttcacgtccg | 2100 |
| gcgaaacgtc gcccaaccgg cggcgtcgag tcactacgcg ccattccgtg gatcttcgcc | 2160 |
| tggacgcaaa accgtctgat gctccccgcc tggctgggtg caggtacggc gctgcaaaaa | 2220 |
| gtggtcgaag acggcaaaca gagcgagctg gaggctatgt gccgcgattg gccattcttc | 2280 |
| tcgacgcgtc tcggcatgct ggagatggtc ttcgccaaag cagacctgtg gctggcggaa | 2340 |
| tactatgacc aacgcctggt agacaaagca ctgtggccgt taggtaaaga gttacgcaac | 2400 |
| ctgcaagaag aagacatcaa agtggtgctg gcgattgcca acgattccca tctgatggcc | 2460 |
| gatctgccgt ggattgcaga gtctattcag ctacggaata tttacaccga cccgctgaac | 2520 |
| gtattgcagg ccgagttgct gcaccgctcc cgccaggcag aaaaagaagg ccaggaaccg | 2580 |
| gatcctcgcg tcgaacaagc gttaatggtc actattgccg ggattgcggc aggtatgcgt | 2640 |

```
aataccggct aa                                                        2652
```

<210> SEQ ID NO 6
<211> LENGTH: 883
<212> TYPE: PRT
<213> ORGANISM: Escherichia coli

<400> SEQUENCE: 6

```
Met Asn Glu Gln Tyr Ser Ala Leu Arg Ser Asn Val Ser Met Leu Gly
 1               5                  10                  15

Lys Val Leu Gly Glu Thr Ile Lys Asp Ala Leu Gly Glu His Ile Leu
             20                  25                  30

Glu Arg Val Glu Thr Ile Arg Lys Leu Ser Lys Ser Ser Arg Ala Gly
         35                  40                  45

Asn Asp Ala Asn Arg Gln Glu Leu Leu Thr Thr Leu Gln Asn Leu Ser
     50                  55                  60

Asn Asp Glu Leu Leu Pro Val Ala Arg Ala Phe Ser Gln Phe Leu Asn
 65                  70                  75                  80

Leu Ala Asn Thr Ala Glu Gln Tyr His Ser Ile Ser Pro Lys Gly Glu
                 85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365
```

```
Gly Ile Ile Ala Asn Gly Asp Leu Leu Asp Thr Leu Arg Val Lys
            370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
            435                 440                 445

Ala Glu Thr Arg Glu Val Leu Asp Thr Cys Gln Val Ile Ala Glu Ala
450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
                500                 505                 510

Asn Ala Asn Asp Val Met Thr Gln Leu Leu Asn Ile Asp Trp Tyr Arg
            515                 520                 525

Gly Leu Ile Gln Gly Lys Gln Met Val Met Ile Gly Tyr Ser Asp Ser
            530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
                580                 585                 590

His Ala Ala Leu Leu Ser Gln Pro Pro Gly Ser Leu Lys Gly Gly Leu
                595                 600                 605

Arg Val Thr Glu Gln Gly Glu Met Ile Arg Phe Lys Tyr Gly Leu Pro
            610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
                660                 665                 670

Arg Glu Asn Lys Asp Phe Val Pro Tyr Phe Arg Ser Ala Thr Pro Glu
            675                 680                 685

Gln Glu Leu Gly Lys Leu Pro Leu Gly Ser Arg Pro Ala Lys Arg Arg
            690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
            755                 760                 765

Met Val Phe Ala Lys Ala Asp Leu Trp Leu Ala Glu Tyr Tyr Asp Gln
            770                 775                 780

Arg Leu Val Asp Lys Ala Leu Trp Pro Leu Gly Lys Glu Leu Arg Asn
785                 790                 795                 800
```

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly

<210> SEQ ID NO 7
<211> LENGTH: 1284
<212> TYPE: DNA
<213> ORGANISM: Escherichia coli

<400> SEQUENCE: 7

```
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tactttttatt    180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg atgttaaca atcctcgtca ccgtgaaatt      480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga acgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aatgctgga agaaatcagc     840
tccgttaaac acattccgga atttgttcgt cgtgcgaaag acaaaaatga ttctttccgc     900
ctgatgggct cggtcaccg cgtgtacaaa aattacgacc gcgcgccac cgtaatgcgt      960
gaaacctgcc atgaagtgct gaaagagctg ggcacgaagg atgacctgct ggaagtggct    1020
atggagctgg aaaacatcgc gctgaacgac ccgtactttta cgagaagaa actgtacccg    1080
aacgtcgatt tctactctgg tatcatcctg aaagcgatgg gtattccgtc ttccatgttc    1140
accgtcattt tcgcaatggc acgtaccgtt ggctggatcg cccactggag cgaaatgcac    1200
agtgacggta tgaagattgc ccgtccgcgt cagctgtata caggatatga aaaacgcgac    1260
tttaaaagcg atatcaagcg ttaa                                           1284
```

<210> SEQ ID NO 8
<211> LENGTH: 427
<212> TYPE: PRT
<213> ORGANISM: Escherichia coli

<400> SEQUENCE: 8

Met Ala Asp Thr Lys Ala Lys Leu Thr Leu Asn Gly Asp Thr Ala Val
1               5                   10                  15

-continued

Glu Leu Asp Val Leu Lys Gly Thr Leu Gly Gln Asp Val Ile Asp Ile
         20                  25                  30

Arg Thr Leu Gly Ser Lys Gly Val Phe Thr Phe Asp Pro Gly Phe Thr
         35                  40                  45

Ser Thr Ala Ser Cys Glu Ser Lys Ile Thr Phe Ile Asp Gly Asp Glu
 50                  55                  60

Gly Ile Leu Leu His Arg Gly Phe Pro Ile Asp Gln Leu Ala Thr Asp
 65                  70                  75                  80

Ser Asn Tyr Leu Glu Val Cys Tyr Ile Leu Leu Asn Gly Glu Lys Pro
                 85                  90                  95

Thr Gln Glu Gln Tyr Asp Glu Phe Lys Thr Val Thr Arg His Thr
                 100                 105                 110

Met Ile His Glu Gln Ile Thr Arg Leu Phe His Ala Phe Arg Arg Asp
         115                 120                 125

Ser His Pro Met Ala Val Met Cys Gly Ile Thr Gly Ala Leu Ala Ala
         130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                 165                 170                 175

Tyr Lys Tyr Ser Ile Gly Gln Pro Phe Val Tyr Pro Arg Asn Asp Leu
                 180                 185                 190

Ser Tyr Ala Gly Asn Phe Leu Asn Met Met Phe Ser Thr Pro Cys Glu
                 195                 200                 205

Pro Tyr Glu Val Asn Pro Ile Leu Glu Arg Ala Met Asp Arg Ile Leu
         210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                 245                 250                 255

Ile Ala Ser Leu Trp Gly Pro Ala His Gly Gly Ala Asn Glu Ala Ala
                 260                 265                 270

Leu Lys Met Leu Glu Glu Ile Ser Ser Val Lys His Ile Pro Glu Phe
         275                 280                 285

Val Arg Arg Ala Lys Asp Lys Asn Asp Ser Phe Arg Leu Met Gly Phe
         290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                 325                 330                 335

Leu Glu Val Ala Met Glu Leu Glu Asn Ile Ala Leu Asn Asp Pro Tyr
                 340                 345                 350

Phe Ile Glu Lys Lys Leu Tyr Pro Asn Val Asp Phe Tyr Ser Gly Ile
         355                 360                 365

Ile Leu Lys Ala Met Gly Ile Pro Ser Ser Met Phe Thr Val Ile Phe
         370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                 405                 410                 415

Glu Lys Arg Asp Phe Lys Ser Asp Ile Lys Arg
                 420                 425

<210> SEQ ID NO 9
<211> LENGTH: 2676
<212> TYPE: DNA
<213> ORGANISM: Escherichia coli

<400> SEQUENCE: 9

| | | | | | |
|---|---|---|---|---|---|
| atgtcgtcaa | ccctacgaga | agccagtaag | gacacgttgc | aggccaaaga | taaaacttac | 60 |
| cactactaca | gcctgccgct | tgctgctaaa | tcactgggcg | atatcacccg | tctacccaag | 120 |
| tcactcaaag | ttttgctcga | aacctgctg | cgctggcagg | atggtaactc | ggttaccgaa | 180 |
| gaggatatcc | acgcgctggc | aggatggctg | aaaaatgccc | atgctgaccg | tgaaattgcc | 240 |
| taccgcccgg | caagggtgct | gatgcaggac | tttaccggcg | tacctgccgt | tgttgatctg | 300 |
| gcggcaatgc | gcgaagcggt | taaacgcctc | ggcggcgata | ctgcaaaggt | taacccgctc | 360 |
| tcaccggtcg | acctggtcat | tgaccactcg | gtgaccgtcg | atcgttttgg | tgatgatgag | 420 |
| gcatttgaag | aaaacgtacg | cctggaaatg | gagcgcaacc | acgaacgtta | tgtgttcctg | 480 |
| aaatggggaa | agcaagcgtt | cagtcggttt | agcgtcgtgc | cgccaggcac | aggcatttgc | 540 |
| catcaggtta | acctcgaata | tctcggcaaa | gcagtgtgga | gtgaattgca | ggacggtgaa | 600 |
| tggattgctt | atccggatac | actcgttggt | actgactcgc | acaccaccat | gatcaacggc | 660 |
| cttggcgtgc | tggggtgggg | cgttggtggg | atcgaagcag | aagccgcaat | gttaggccag | 720 |
| ccggtttcca | tgcttatccc | ggatgtagtg | ggcttcaaac | ttaccggaaa | attacgtgaa | 780 |
| ggtattaccg | ccacagacct | ggttctcact | gttacccaaa | tgctgcgcaa | acatggcgtg | 840 |
| gtggggaaat | cgtcgaatt | ttatggtgat | ggtctggatt | cactaccgtt | ggcggatcgc | 900 |
| gccaccattg | ccaatatgtc | gccagaatat | ggtgccacct | gtggcttctt | cccaatcgat | 960 |
| gctgtaaccc | tcgattacat | gcgtttaagc | gggcgcagcg | aagatcaggt | cgagttggtc | 1020 |
| gaaaaatatg | ccaaagcgca | gggcatgtgg | cgtaacccgg | gcgatgaacc | aatttttacc | 1080 |
| agtacgttag | aactggatat | gaatgacgtt | gaagcgagcc | tggcagggcc | taaacgccca | 1140 |
| caggatcgcg | ttgcactgcc | cgatgtacca | aaagcatttg | ccgccagtaa | cgaactggaa | 1200 |
| gtgaatgcca | cgcataaaga | tcgccagccg | gtcgattatg | ttatgaacgg | acatcagtat | 1260 |
| cagttacctg | atggcgctgt | ggtcattgct | gcgataacct | cgtgcaccaa | cacctctaac | 1320 |
| ccaagtgtgc | tgatggccgc | aggcttgctg | gcgaaaaaag | ccgtaactct | gggcctcaag | 1380 |
| cggcaaccat | gggtcaaagc | gtcgctggca | ccgggttcga | agtcgtttc | tgattatctg | 1440 |
| gcaaaagcga | aactgacacc | gtatctcgac | gaactggggt | ttaaccttgt | gggatacggt | 1500 |
| tgtaccacct | gtattggtaa | ctctgggccg | ctgcccgatc | ctatcgaaac | ggcaatcaaa | 1560 |
| aaaagcgatt | taaccgtcgg | tgcggtgctg | tccggcaacc | gtaactttga | aggccgtatc | 1620 |
| catccgctgg | ttaaaactaa | ctggctggcc | tcgccgccgc | tggtggttgc | ctatgcgctg | 1680 |
| gcggaaaata | tgaatatcaa | cctggcttct | gagcctatcg | gccatgatcg | caaaggcgat | 1740 |
| ccggtttatc | tgaaagatat | ctggccatcg | gcacaagaaa | ttgcccgtgc | ggtagaacaa | 1800 |
| gtctccacag | aaatgttccg | caaagagtac | gcagaagttt | ttgaaggcac | agcagagtgg | 1860 |
| aagggaatta | acgtcacacg | atccgatacc | tacggttggc | aggaggactc | aacctatatt | 1920 |
| cgcttatcgc | ctttctttga | tgaaatgcag | gcaacaccag | caccagtgga | agatattcac | 1980 |
| ggtgcgcgga | tcctcgcaat | gctggggat | tcagtcacca | ctgaccatat | ctctccggcg | 2040 |
| ggcagtatta | gcccgacag | cccagcgggt | cgatatctac | aaggtcgggg | tgttgagcga | 2100 |
| aaagacttta | actcctacgg | ttcgcggcgt | ggtaaccatg | aagtgatgat | gcgcggcacc | 2160 |
| ttcgccaata | ttcgcatccg | taatgaaatg | gtgcctggcg | ttgaagggg | gatgacgcgg | 2220 |

-continued

```
catttacctg acagcgacgt agtctctatt tatgatgctg cgatgcgcta taagcaggag    2280
caaacgccgc tggcggtgat tgccgggaaa gagtatggat caggctccag tcgtgactgg    2340
gcggcaaaag gtccgcgtct gcttggtatt cgtgtggtga ttgccgaatc gtttgaacga    2400
attcaccgtt cgaatttaat tggcatgggc atcctgccgc tggaatttcc gcaaggcgta    2460
acgcgtaaaa cgttagggct aaccggggaa gagaagattg atattggcga tctgcaaaac    2520
ctacaacccg cgcgacggt tccggtgacg cttacgcgcg cggatggtag ccaggaagtc    2580
gtaccctgcc gttgtcgtat cgacaccgcg acggagttga cctactacca gaacgacggc    2640
attttgcatt atgtcattcg taatatgttg aagtaa                             2676
```

<210> SEQ ID NO 10
<211> LENGTH: 891
<212> TYPE: PRT
<213> ORGANISM: Escherichia coli

<400> SEQUENCE: 10

```
Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
            20                  25                  30

Gly Asp Ile Thr Arg Leu Pro Lys Ser Leu Lys Val Leu Leu Glu Asn
        35                  40                  45

Leu Leu Arg Trp Gln Asp Gly Asn Ser Val Thr Glu Glu Asp Ile His
    50                  55                  60

Ala Leu Ala Gly Trp Leu Lys Asn Ala His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
            100                 105                 110

Asp Thr Ala Lys Val Asn Pro Leu Ser Pro Val Asp Leu Val Ile Asp
        115                 120                 125

His Ser Val Thr Val Asp Arg Phe Gly Asp Asp Glu Ala Phe Glu Glu
    130                 135                 140

Asn Val Arg Leu Glu Met Glu Arg Asn His Glu Arg Tyr Val Phe Leu
145                 150                 155                 160

Lys Trp Gly Lys Gln Ala Phe Ser Arg Phe Ser Val Val Pro Pro Gly
                165                 170                 175

Thr Gly Ile Cys His Gln Val Asn Leu Glu Tyr Leu Gly Lys Ala Val
            180                 185                 190

Trp Ser Glu Leu Gln Asp Gly Glu Trp Ile Ala Tyr Pro Asp Thr Leu
        195                 200                 205

Val Gly Thr Asp Ser His Thr Thr Met Ile Asn Gly Leu Gly Val Leu
    210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Asp Ser Leu Pro Leu Ala Asp Arg Ala Thr Ile Ala
```

```
                290                 295                 300
Asn Met Ser Pro Glu Tyr Gly Ala Thr Cys Gly Phe Phe Pro Ile Asp
305                 310                 315                 320

Ala Val Thr Leu Asp Tyr Met Arg Leu Ser Gly Arg Ser Glu Asp Gln
                325                 330                 335

Val Glu Leu Val Glu Lys Tyr Ala Lys Ala Gln Gly Met Trp Arg Asn
                340                 345                 350

Pro Gly Asp Glu Pro Ile Phe Thr Ser Thr Leu Glu Leu Asp Met Asn
                355                 360                 365

Asp Val Glu Ala Ser Leu Ala Gly Pro Lys Arg Pro Gln Asp Arg Val
370                 375                 380

Ala Leu Pro Asp Val Pro Lys Ala Phe Ala Ala Ser Asn Glu Leu Glu
385                 390                 395                 400

Val Asn Ala Thr His Lys Asp Arg Gln Pro Val Asp Tyr Val Met Asn
                405                 410                 415

Gly His Gln Tyr Gln Leu Pro Asp Gly Ala Val Ile Ala Ala Ile
                420                 425                 430

Thr Ser Cys Thr Asn Thr Ser Asn Pro Ser Val Leu Met Ala Ala Gly
                435                 440                 445

Leu Leu Ala Lys Lys Ala Val Thr Leu Gly Leu Lys Arg Gln Pro Trp
450                 455                 460

Val Lys Ala Ser Leu Ala Pro Gly Ser Lys Val Val Ser Asp Tyr Leu
465                 470                 475                 480

Ala Lys Ala Lys Leu Thr Pro Tyr Leu Asp Glu Leu Gly Phe Asn Leu
                485                 490                 495

Val Gly Tyr Gly Cys Thr Thr Cys Ile Gly Asn Ser Gly Pro Leu Pro
                500                 505                 510

Asp Pro Ile Glu Thr Ala Ile Lys Lys Ser Asp Leu Thr Val Gly Ala
                515                 520                 525

Val Leu Ser Gly Asn Arg Asn Phe Glu Gly Arg Ile His Pro Leu Val
                530                 535                 540

Lys Thr Asn Trp Leu Ala Ser Pro Pro Leu Val Val Ala Tyr Ala Leu
545                 550                 555                 560

Ala Gly Asn Met Asn Ile Asn Leu Ala Ser Glu Pro Ile Gly His Asp
                565                 570                 575

Arg Lys Gly Asp Pro Val Tyr Leu Lys Asp Ile Trp Pro Ser Ala Gln
                580                 585                 590

Glu Ile Ala Arg Ala Val Glu Gln Val Ser Thr Glu Met Phe Arg Lys
                595                 600                 605

Glu Tyr Ala Glu Val Phe Glu Gly Thr Ala Glu Trp Lys Gly Ile Asn
                610                 615                 620

Val Thr Arg Ser Asp Thr Tyr Gly Trp Gln Glu Asp Ser Thr Tyr Ile
625                 630                 635                 640

Arg Leu Ser Pro Phe Phe Asp Glu Met Gln Ala Thr Pro Ala Pro Val
                645                 650                 655

Glu Asp Ile His Gly Ala Arg Ile Leu Ala Met Leu Gly Asp Ser Val
                660                 665                 670

Thr Thr Asp His Ile Ser Pro Ala Gly Ser Ile Lys Pro Asp Ser Pro
                675                 680                 685

Ala Gly Arg Tyr Leu Gln Gly Arg Gly Val Glu Arg Lys Asp Phe Asn
                690                 695                 700

Ser Tyr Gly Ser Arg Arg Gly Asn His Glu Val Met Met Arg Gly Thr
705                 710                 715                 720
```

```
Phe Ala Asn Ile Arg Ile Arg Asn Glu Met Val Pro Gly Val Glu Gly
                725                 730                 735
Gly Met Thr Arg His Leu Pro Asp Ser Asp Val Ser Ile Tyr Asp
            740                 745                 750
Ala Ala Met Arg Tyr Lys Gln Glu Gln Thr Pro Leu Ala Val Ile Ala
        755                 760                 765
Gly Lys Glu Tyr Gly Ser Gly Ser Ser Arg Asp Trp Ala Ala Lys Gly
    770                 775                 780
Pro Arg Leu Leu Gly Ile Arg Val Val Ile Ala Glu Ser Phe Glu Arg
785                 790                 795                 800
Ile His Arg Ser Asn Leu Ile Gly Met Gly Ile Leu Pro Leu Glu Phe
                805                 810                 815
Pro Gln Gly Val Thr Arg Lys Thr Leu Gly Leu Thr Gly Glu Glu Lys
            820                 825                 830
Ile Asp Ile Gly Asp Leu Gln Asn Leu Gln Pro Gly Ala Thr Val Pro
        835                 840                 845
Val Thr Leu Thr Arg Ala Asp Gly Ser Gln Glu Val Val Pro Cys Arg
    850                 855                 860
Cys Arg Ile Asp Thr Ala Thr Glu Leu Thr Tyr Tyr Gln Asn Asp Gly
865                 870                 875                 880
Ile Leu His Tyr Val Ile Arg Asn Met Leu Lys
                885                 890

<210> SEQ ID NO 11
<211> LENGTH: 2598
<212> TYPE: DNA
<213> ORGANISM: Escherichia coli

<400> SEQUENCE: 11
atgctagaag aataccgtaa gcacgtagct gagcgtgccg ctgagggat tgcgcccaaa      60
cccctggatg caaaccaaat ggccgcactt gtagagctgc tgaaaaaccc gcccgcgggc    120
gaagaagaat tcctgttaga tctgttaacc aaccgtgttc ccccaggcgt cgatgaagcc    180
gcctatgtca agcaggcttc ctggctgct atcgcgaaag gcgaagccaa atcccctctg     240
ctgactccgg aaaaagccat cgaactgctg ggcaccatgc agggtggtta acacattcat    300
ccgctgatcg acgcgctgga tgatgccaaa ctggcaccta ttgctgccaa gcactttct    360
cacacgctgc tgatgttcga taacttctat gacgtagaag agaaagcgaa agcaggcaac    420
gaatatgcga agcaggttat gcagtcctgg cggatgccg aatggttcct gaatcgcccg    480
gcgctggctg aaaaactgac cgttactgtc ttcaaagtca ctggcgaaac taacaccgat    540
gacctttctc cggcaccgga tgcgtggtca cgcccggata tcccactgca cgcgctggcg    600
atgctgaaaa acgcccgtga aggtattgag ccagaccagc tggtgttgt tggtccgatc    660
aagcaaatcg aagctctgca acagaaaggt ttcccgctgg cgtacgtcgg tgacgttgtg    720
ggtacgggtt cttcgcgtaa atccgccact aactccgttc tgtggttat gggcgatgat    780
attccacatg tgccgaacaa acgcggcggt ggtttgtgcc tcggcggtaa aattgcaccc    840
atcttcttta cacgatgga gacgcgggt gcactgccaa tcgaagtcga cgtctctaac    900
ctgaacatgg cgacgtgat tgacgtttac ccgtacaaag gtgaagtgcg taaccacgaa    960
accggcgaac tgctggcgac cttcgaactg aaaaccgacg tgctgattga tgaagtgcgt   1020
gctggtggcc gtattccgct gattatcggg cgtggcctga ccaccaaagc gcgtgaagca   1080
cttggtctgc gcacagtga tgtgttccgt caggcgaaaa tgtcgctga gagcgatcgc    1140
ggcttctcgc tggcgcaaaa aatggtaggc cgtgcctgtg gcgtgaaagg cattcgtccg   1200
```

```
ggcgcgtact gtgaaccgaa aatgacttct gtaggttccc aggacaccac cggcccgatg    1260
acccgtgatg aactgaaaga cctggcgtgc ctgggcttct cggctgacct ggtgatgcag    1320
tctttctgcc acaccgcggc gtatccgaag ccagttgacg tgaacacgca ccacacgctg    1380
ccggacttca ttatgaaccg tggcggtgtg tcgctgcgtc cgggtgacgg cgtcattcac    1440
tcctggctga accgtatgct gctgccggat ccgtcggta ccggtggtga ctcccatacc    1500
cgtttcccga tcggtatctc tttcccggcg ggttctggtc tggtggcgtt tgctgccgca    1560
actggcgtaa tgccgcttga tatgccggaa tccgttctgg tgcgcttcaa aggcaaaatg    1620
cagccgggca tcaccctgcg cgatctggta cacgctattc cgctgtatgc gatcaaacaa    1680
ggtctgctga ccgttgagaa gaaaggcaag aaaaacatct tctctggccg catcctggaa    1740
attgaaggtc tgccggatct gaaagttgag caggcctttg agctaaccga tgcgtccgcc    1800
gagcgttctg ccgctggttg taccatcaag ctgaacaaag aaccgatcat cgaatacctg    1860
aactctaaca tcgtcctgct gaagtggatg atcgcggaag gttacggcga tcgtcgtacc    1920
ctggaacgtc gtattcaggg catggaaaaa tggctggcga atcctgagct gctggaagcc    1980
gatgcagatg cggaatacgc ggcagtgatc gacatcgatc tggcggatat taaagagcca    2040
atcctgtgtg ctccgaacga cccggatgac gcgcgtccgc tgtctgcggt acagggtgag    2100
aagatcgacg aagtgtttat cggttcctgc atgaccaaca tcggtcactt ccgtgctgcg    2160
ggtaaactgc tggatgcgca taaggtcag ttgccgaccc gcctgtgggt ggcaccgcca    2220
acccgtatgg acgccgcaca gttgaccgaa gaaggctact acagcgtctt cggtaagagt    2280
ggtgcgcgta tcgagatccc tggctgttcc ctgtgtatgg gtaaccaggc gcgtgtggcg    2340
gacggtgcaa cggtggtttc cacctctacc cgtaacttcc cgaaccgtct gggtactggc    2400
gcgaatgtct tcctggcttc tgcggaactg gcggctgttg cggcgctgat ggcaaactg    2460 ccgacgccgg aagagtacca gacctacgtg gcgcaggtag ataaaacagc cgttgatact    2520
taccgttatc tgaacttcaa ccagctttct cagtacaccg agaaagccga tggggtgatt    2580
ttccagactg cggtttaa                                                  2598
```

<210> SEQ ID NO 12
<211> LENGTH: 865
<212> TYPE: PRT
<213> ORGANISM: Escherichia coli

<400> SEQUENCE: 12

```
Met Leu Glu Glu Tyr Arg Lys His Val Ala Glu Arg Ala Ala Glu Gly
1               5                   10                  15

Ile Ala Pro Lys Pro Leu Asp Ala Asn Gln Met Ala Ala Leu Val Glu
            20                  25                  30

Leu Leu Lys Asn Pro Pro Ala Gly Glu Glu Glu Phe Leu Leu Asp Leu
        35                  40                  45

Leu Thr Asn Arg Val Pro Pro Gly Val Asp Glu Ala Ala Tyr Val Lys
    50                  55                  60

Ala Gly Phe Leu Ala Ala Ile Ala Lys Gly Glu Ala Lys Ser Pro Leu
65                  70                  75                  80

Leu Thr Pro Glu Lys Ala Ile Glu Leu Leu Gly Thr Met Gln Gly Gly
                85                  90                  95

Tyr Asn Ile His Pro Leu Ile Asp Ala Leu Asp Asp Ala Lys Leu Ala
            100                 105                 110

Pro Ile Ala Ala Lys Ala Leu Ser His Thr Leu Leu Met Phe Asp Asn
        115                 120                 125
```

```
Phe Tyr Asp Val Glu Glu Lys Ala Lys Ala Gly Asn Glu Tyr Ala Lys
    130                 135                 140
Gln Val Met Gln Ser Trp Ala Asp Ala Glu Trp Phe Leu Asn Arg Pro
145                 150                 155                 160
Ala Leu Ala Glu Lys Leu Thr Val Thr Val Phe Lys Val Thr Gly Glu
                165                 170                 175
Thr Asn Thr Asp Asp Leu Ser Pro Ala Pro Asp Ala Trp Ser Arg Pro
            180                 185                 190
Asp Ile Pro Leu His Ala Leu Ala Met Leu Lys Asn Ala Arg Glu Gly
        195                 200                 205
Ile Glu Pro Asp Gln Pro Gly Val Val Gly Pro Ile Lys Gln Ile Glu
    210                 215                 220
Ala Leu Gln Gln Lys Gly Phe Pro Leu Ala Tyr Val Gly Asp Val Val
225                 230                 235                 240
Gly Thr Gly Ser Ser Arg Lys Ser Ala Thr Asn Ser Val Leu Trp Phe
                245                 250                 255
Met Gly Asp Asp Ile Pro His Val Pro Asn Lys Arg Gly Gly Gly Leu
            260                 265                 270
Cys Leu Gly Gly Lys Ile Ala Pro Ile Phe Phe Asn Thr Met Glu Asp
        275                 280                 285
Ala Gly Ala Leu Pro Ile Glu Val Asp Val Ser Asn Leu Asn Met Gly
    290                 295                 300
Asp Val Ile Asp Val Tyr Pro Tyr Lys Gly Glu Val Arg Asn His Glu
305                 310                 315                 320
Thr Gly Glu Leu Leu Ala Thr Phe Glu Leu Lys Thr Asp Val Leu Ile
                325                 330                 335
Asp Glu Val Arg Ala Gly Gly Arg Ile Pro Leu Ile Ile Gly Arg Gly
            340                 345                 350
Leu Thr Thr Lys Ala Arg Glu Ala Leu Gly Leu Pro His Ser Asp Val
        355                 360                 365
Phe Arg Gln Ala Lys Asp Val Ala Glu Ser Asp Arg Gly Phe Ser Leu
    370                 375                 380
Ala Gln Lys Met Val Gly Arg Ala Cys Gly Val Lys Gly Ile Arg Pro
385                 390                 395                 400
Gly Ala Tyr Cys Glu Pro Lys Met Thr Ser Val Gly Ser Gln Asp Thr
                405                 410                 415
Thr Gly Pro Met Thr Arg Asp Glu Leu Lys Asp Leu Ala Cys Leu Gly
            420                 425                 430
Phe Ser Ala Asp Leu Val Met Gln Ser Phe Cys His Thr Ala Ala Tyr
        435                 440                 445
Pro Lys Pro Val Asp Val Asn Thr His His Thr Leu Pro Asp Phe Ile
    450                 455                 460
Met Asn Arg Gly Gly Val Ser Leu Arg Pro Gly Asp Gly Val Ile His
465                 470                 475                 480
Ser Trp Leu Asn Arg Met Leu Leu Pro Asp Thr Val Gly Thr Gly Gly
                485                 490                 495
Asp Ser His Thr Arg Phe Pro Ile Gly Ile Ser Phe Pro Ala Gly Ser
            500                 505                 510
Gly Leu Val Ala Phe Ala Ala Thr Gly Val Met Pro Leu Asp Met
        515                 520                 525
Pro Glu Ser Val Leu Val Arg Phe Lys Gly Lys Met Gln Pro Gly Ile
    530                 535                 540
Thr Leu Arg Asp Leu Val His Ala Ile Pro Leu Tyr Ala Ile Lys Gln
```

-continued

```
            545                 550                 555                 560
Gly Leu Leu Thr Val Glu Lys Lys Gly Lys Lys Asn Ile Phe Ser Gly
                    565                 570                 575
Arg Ile Leu Glu Ile Glu Gly Leu Pro Asp Leu Lys Val Glu Gln Ala
                580                 585                 590
Phe Glu Leu Thr Asp Ala Ser Ala Glu Arg Ser Ala Ala Gly Cys Thr
            595                 600                 605
Ile Lys Leu Asn Lys Glu Pro Ile Ile Glu Tyr Leu Asn Ser Asn Ile
        610                 615                 620
Val Leu Leu Lys Trp Met Ile Ala Glu Gly Tyr Gly Asp Arg Arg Thr
625                 630                 635                 640
Leu Glu Arg Arg Ile Gln Gly Met Glu Lys Trp Leu Ala Asn Pro Glu
                    645                 650                 655
Leu Leu Glu Ala Asp Ala Asp Ala Glu Tyr Ala Ala Val Ile Asp Ile
                660                 665                 670
Asp Leu Ala Asp Ile Lys Glu Pro Ile Leu Cys Ala Pro Asn Asp Pro
            675                 680                 685
Asp Asp Ala Arg Pro Leu Ser Ala Val Gln Gly Glu Lys Ile Asp Glu
        690                 695                 700
Val Phe Ile Gly Ser Cys Met Thr Asn Ile Gly His Phe Arg Ala Ala
705                 710                 715                 720
Gly Lys Leu Leu Asp Ala His Lys Gly Gln Leu Pro Thr Arg Leu Trp
                    725                 730                 735
Val Ala Pro Pro Thr Arg Met Asp Ala Ala Gln Leu Thr Glu Glu Gly
                740                 745                 750
Tyr Tyr Ser Val Phe Gly Lys Ser Gly Ala Arg Ile Glu Ile Pro Gly
            755                 760                 765
Cys Ser Leu Cys Met Gly Asn Gln Ala Arg Val Ala Asp Gly Ala Thr
        770                 775                 780
Val Val Ser Thr Ser Thr Arg Asn Phe Pro Asn Arg Leu Gly Thr Gly
785                 790                 795                 800
Ala Asn Val Phe Leu Ala Ser Ala Glu Leu Ala Ala Val Ala Ala Leu
                    805                 810                 815
Ile Gly Lys Leu Pro Thr Pro Glu Glu Tyr Gln Thr Tyr Val Ala Gln
                820                 825                 830
Val Asp Lys Thr Ala Val Asp Thr Tyr Arg Tyr Leu Asn Phe Asn Gln
            835                 840                 845
Leu Ser Gln Tyr Thr Glu Lys Ala Asp Gly Val Ile Phe Gln Thr Ala
        850                 855                 860
Val
865
```